(12) United States Patent
Ben Yahia et al.

(10) Patent No.: US 12,077,796 B2
(45) Date of Patent: Sep. 3, 2024

(54) CELL CULTURE METHODS

(71) Applicant: UCB BIOPHARMA SRL, Brussels (BE)

(72) Inventors: Bassem Ben Yahia, Brussels (BE); Laetitia Malphettes, Brussels (BE); Nadine Kochanowski, Brussels (BE); Gill Renner, Slough (GB); Sandrine Durran, Slough (GB); Andrew Jeffrey Yates, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 752 days.

(21) Appl. No.: 16/615,419

(22) PCT Filed: May 29, 2018

(86) PCT No.: PCT/EP2018/064102
§ 371 (c)(1),
(2) Date: Nov. 21, 2019

(87) PCT Pub. No.: WO2018/219968
PCT Pub. Date: Dec. 6, 2018

(65) Prior Publication Data
US 2020/0239923 A1 Jul. 30, 2020

(30) Foreign Application Priority Data
May 31, 2017 (GB) ..................... 1708655

(51) Int. Cl.
*C12P 21/02* (2006.01)
*C07K 1/16* (2006.01)
*C07K 16/00* (2006.01)
*C12N 5/00* (2006.01)

(52) U.S. Cl.
CPC ............... *C12P 21/02* (2013.01); *C07K 1/16* (2013.01); *C07K 16/00* (2013.01); *C12N 5/0018* (2013.01); *C07K 2317/14* (2013.01); *C07K 2317/565* (2013.01); *C12N 2500/32* (2013.01); *C12N 2510/02* (2013.01); *C12N 2511/00* (2013.01); *C12N 2523/00* (2013.01)

(58) Field of Classification Search
CPC .............................. C07K 16/00; C12N 5/0018
See application file for complete search history.

(56) References Cited

U.S. PATENT DOCUMENTS

| | | | |
|---|---|---|---|
| 8,030,027 B2 * | 10/2011 | Shimizu ................ | C07K 16/00 435/70.1 |
| 8,765,413 B2 | 7/2014 | Joosten et al. | |
| 10,196,665 B2 * | 2/2019 | Cheng ................ | C12P 21/00 |
| 10,233,243 B2 | 3/2019 | Finney et al. | |
| 11,555,175 B2 | 1/2023 | Williams et al. | |
| 2006/0148074 A1 | 7/2006 | Gorfien et al. | |
| 2013/0281355 A1 | 10/2013 | Vijayasankaran et al. | |
| 2018/0030495 A1 * | 2/2018 | Cheng ................ | C12N 5/0037 |
| 2020/0048346 A1 | 2/2020 | Yates et al. | |

FOREIGN PATENT DOCUMENTS

| | | | | |
|---|---|---|---|---|
| EP | 2 351 833 | | 8/2011 | |
| WO | WO 98/08934 | | 3/1998 | |
| WO | WO 2008/063892 | | 5/2008 | |
| WO | WO 2011/133902 | | 10/2011 | |
| WO | WO 2011/134921 | | 11/2011 | |
| WO | WO 2012/145682 | | 10/2012 | |
| WO | WO 2013/148686 | | 10/2013 | |
| WO | WO 2013/158275 | | 10/2013 | |
| WO | WO-2013171156 A1 * | 11/2013 | ........... C07K 16/283 |
| WO | WO 2014/019727 | | 2/2014 | |
| WO | WO 2014/145091 | | 9/2014 | |
| WO | WO 2016/108765 | | 7/2016 | |
| WO | WO 2016/180765 | | 11/2016 | |
| WO | WO 2017/186654 | | 11/2017 | |
| WO | WO 2017/194646 | | 11/2017 | |

OTHER PUBLICATIONS

GeneScript. Downloaded Oct. 27, 2022; 6 steps to optimize your recombinant antibody production. On the web at www.genscript.com/gsfiles/techfiles/White-Paper-6-Steps-to-Optimize-Your-Recombinant-Antibody-Expression.pdf. pp. 1-15.*
Bolli R et al. L-proline reduces IgG dimer content and enhances the stability of intravenous immunoglobulin solutions. 2010. Biologicals. 38:150-157. (Year: 2010).*
Patrone, M. et al. "Enhanced Expression of Full-Length Human Cytomegalovirus Fusion Protein in Non-Swelling Baculovirus-Infected Cells with a Minimal Fed-Batch Strategy" *PLOS One*, Mar. 4, 2014, pp. 1-13, vol. 9, No. 3, e90753.
Liu, H. et al. "Impact of cell culture on recombinant monoclonal antibody product heterogeneity" *Biotechnology Progress*, Sep. 1, 2016, pp. 1103-1112, vol. 32, No. 5.
Ben Yahia, B. et al. "Segmented Linear Modeling of CHO Fed-Batch Culture and Its Application to Large Scale Production" *Biotechnology and Bioengineering*, Apr. 1, 2017, pp. 785-797, vol. 114, No. 4.
International Search Report and Written Opinion in International Application No. PCT/EP2018/064102, Nov. 13, 2018, pp. 1-14.
Search Report in International Application No. GB1708655.4, Mar. 7, 2018, pp. 1-5.

(Continued)

*Primary Examiner* — Paul J Holland

(74) *Attorney, Agent, or Firm* — SALIWANCHIK, LLOYD & EISENSCHENK

(57) ABSTRACT

The present invention relates to the use of limited amounts of cysteine and tryptophan in the cell culture medium during production of recombinant proteins, and in particular antibodies. Proteins and antibodies produced under such controlled conditions exhibit reduced heterogeneity, in particular reduced charge variants heterogeneity.

20 Claims, 15 Drawing Sheets

Specification includes a Sequence Listing.

(56) References Cited

OTHER PUBLICATIONS

Hecklau, C. et al. "S-Sulfocysteine simplifies fed-batch processes and increases the CHO specific productivity via anti-oxidant activity" *Journal of Biotechnology*, 2016, pp. 53-63, vol. 218.

Zang, L. et al. "Metabolomics Profiling of Cell Culture Media Leading to the Identification of Riboflavin Photosensitized Degradation of Tryptophan Causing Slow Growth in Cell Culture" *Analytical Chemistry*, May 31, 2011, pp. 5422-5430, vol. 83.

Purdie, J. L. et al. "Cell Culture Media Impact on Drug Product Solution Stability" *Biotechnol. Prog.*, 2016, pp. 1-11.

Banks, D. D. et al. "The Effect of Sucrose Hydrolysis on the Stability of Protein Therapeutics during Accelerated Formulation Studies" *Journal of Pharmaceutical Sciences*, Dec. 2009, pp. 4501-4510, vol. 98, No. 12.

Kshirsagar, R. et al. "Controlling Trisulfide Modification in Recombinant Monoclonal Antibody Produced in Fed-Batch Cell Culture" *Biotechnology and Bioengineering*, Oct. 2012, pp. 2523-2532, vol. 109, No. 10.

Falconer, R. J. et al. "Stabilization of a monoclonal antibody during purification and formulation by addition of basic amino acid excipients" *Journal of Chemical Technology & Biotechnology*, published online Jun. 7, 2011, pp. 942-948, vol. 86.

Ben Yahia, B. et al. "Macroscopic modeling of mammalian cell growth and metabolism" *Applied Microbiology and Biotechnology*, published online Jul. 22, 2015, pp. 7009-7024, vol. 99.

Hazeltine, L. B. et al. "Chemically Defined Media Modifications to Lower Tryptophan Oxidation of Biopharmaceuticals" *Biotechnology Progress*, published online Dec. 7, 2015, pp. 178-188, vol. 32, No. 1.

Jing, Y. et al. "Identification of cell culture conditions to control protein aggregation of IgG fusion proteins expressed in Chinese hamster ovary cells" *Process Biochemistry*, published online Oct. 18, 2011, pp. 69-75, vol. 47.

Seibel, R. et al. "Impact of S-sulfocysteine on fragments and trisulfide bond linkages in monoclonal antibodies" *mAbs*, 2017, pp. 889-897, vol. 9, No. 6.

Zhang, J. "Mammalian Cell Culture for Biopharmaceutical Production" *Manual of Industrial Microbiology and Biotechnology, Fermentation and Cell Culture*, published Mar. 25, 2010, pp. 157-178, No. 3.

* cited by examiner

FIG. 1A

Quantity Cys added = $C_{cys}*F + C_{cys2}*V$

F = feed volume added (L)

$C_{cys}$ = feed concentration (Cys) (g/L)

V = bioreactor volume (L)

$C_{cys2}$ = medium concentration (Cys) (g/L)

FIG. 1B

Quantity RC produced = $C_{RC}*V_F$

RC = recombinant polypeptide $V_F$ = final bioreactor volume (L)

$C_{RC}$ = final RC titer (g/L)

FIG. 1C

Ratio Cys/RC% = Quantity Cys added*100/Quantity RC produced

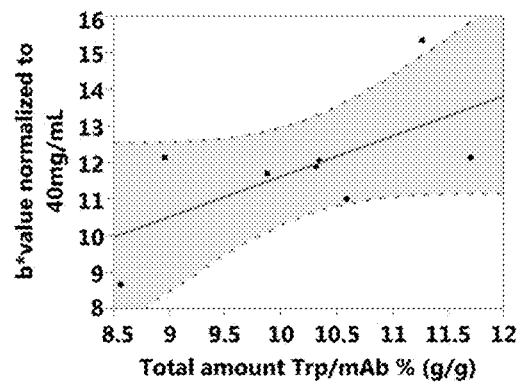 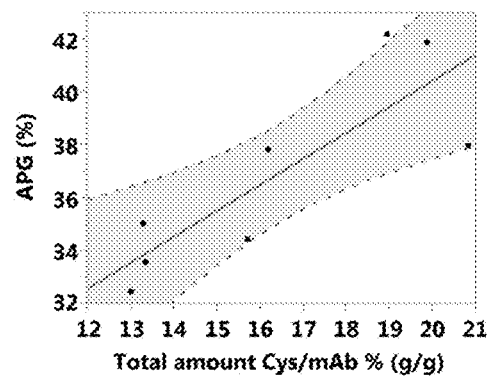
FIG. 2A  FIG. 2B
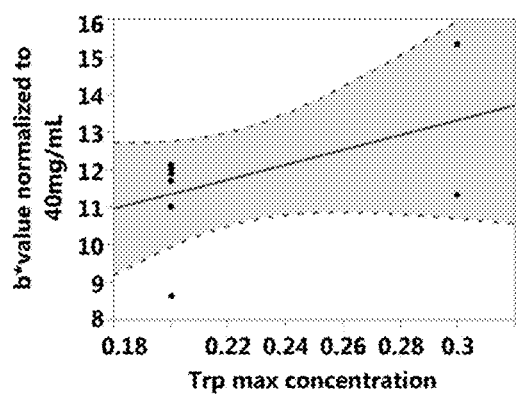 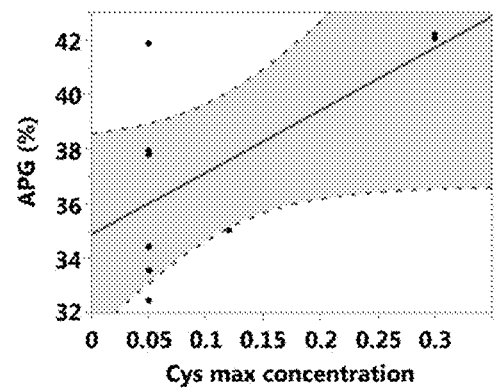
FIG. 2C  FIG. 2D

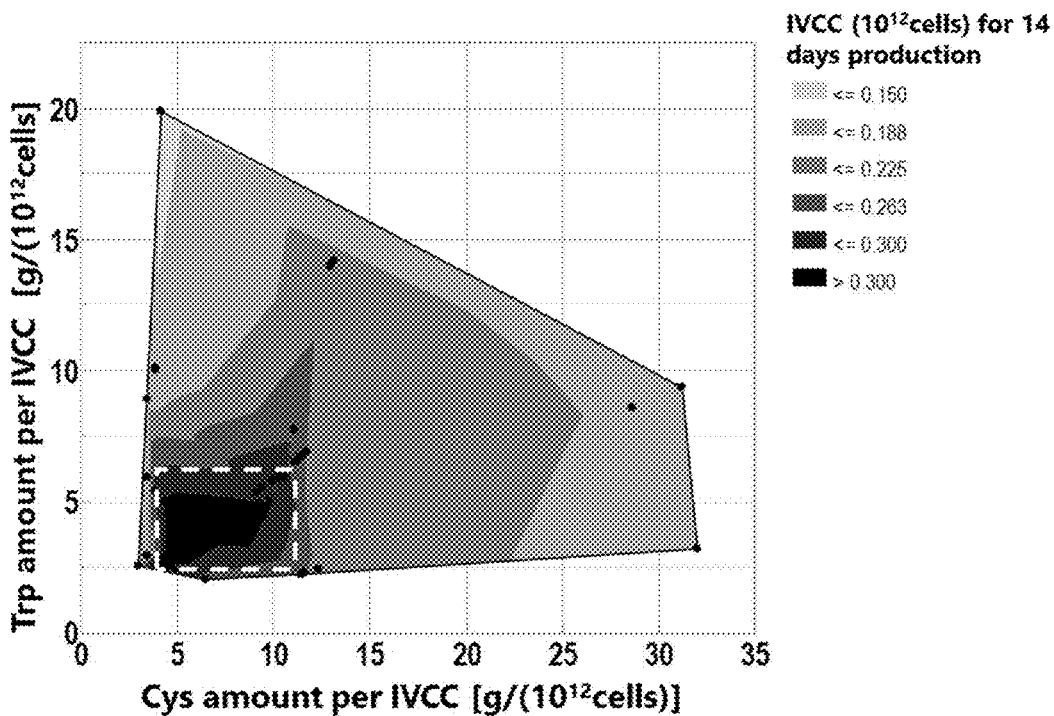
FIG. 11A
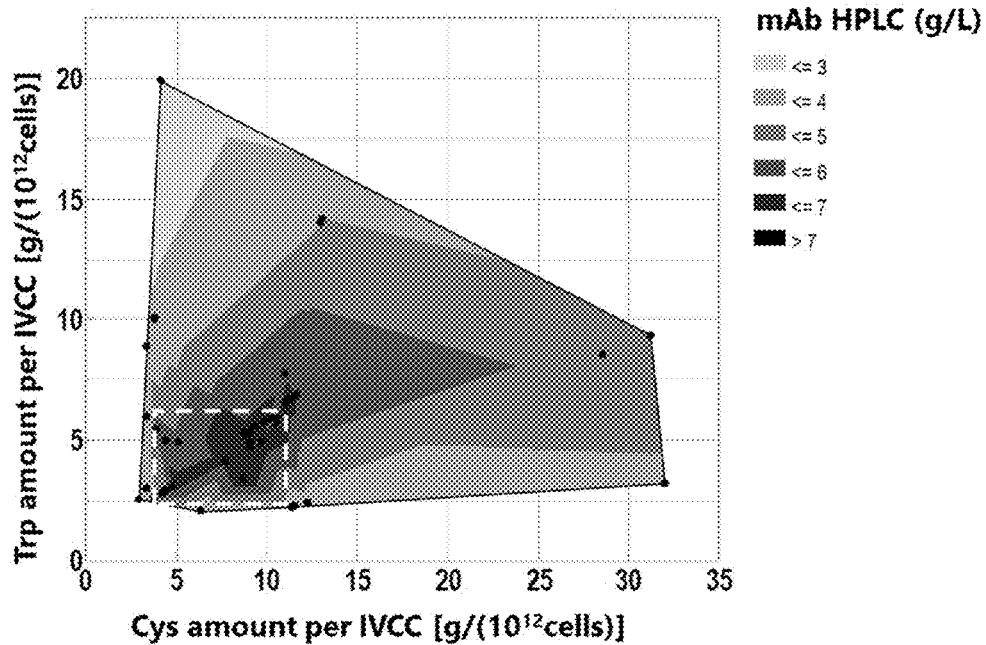
FIG. 11B
$$Cys\ amount\ per\ IVCC = \frac{Quantity\ Cys\ added}{IVCC * 10^{-12}}$$
$$Trp\ amount\ per\ IVCC = \frac{Quantity\ Trp\ added}{IVCC * 10^{-12}}$$
FIG. 11C $$APG\ (\%) = \frac{RATIO\ Cys/RC\% * 70.76}{RATIO\ Cys/RC\% + 47.53} + \frac{RATIO\ Trp/RC\% * 3}{RATIO\ Trp/RC\% + 1} + 17$$

SEQUENCE LISTING

<160> NUMBER OF SEQ ID NOS: 11

<210> SEQ ID NO 1

```
<211> LENGTH: 10
<212> TYPE: PRT
<213> ORGANISM: Artificial Sequence
<220> FEATURE:
<223> OTHER INFORMATION: Humanized

<400> SEQUENCE: 1

Gly Phe Thr Phe Ser Asn Tyr Gly Met Val
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Humanised

<400> SEQUENCE: 2

Tyr Ile Asp Ser Asp Gly Asp Asn Thr Tyr Tyr Arg Asp Ser Val Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: Huminazed

<400> SEQUENCE: 3

Gly Ile Val Arg Pro Phe Leu Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: Humanized

<400> SEQUENCE: 4

Lys Ser Ser Gln Ser Leu Val Gly Ala Ser Gly Lys Thr Tyr Leu Tyr
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Humanized

<400> SEQUENCE: 5

Leu Val Ser Thr Leu Asp Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Humanized

<400> SEQUENCE: 6

Leu Gln Gly Thr His Phe Pro His Thr
1               5
```

<210> SEQ ID NO 7
<211> LENGTH: 112
<212> TYPE: PRT
<213> ORGANISM: Artificial Sequence
<220> FEATURE:
<223> OTHER INFORMATION: Humanized

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30

Ser Gly Lys Thr Tyr Leu Tyr Trp Leu Phe Gln Lys Pro Gly Lys Ala
        35                  40                  45

Pro Lys Arg Leu Ile Tyr Leu Val Ser Thr Leu Asp Ser Gly Ile Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Phe Pro His Thr Phe Gly Gln Gly Thr Lys Leu Glu Ile Lys
            100                 105                 110
```

<210> SEQ ID NO 8
<211> LENGTH: 116
<212> TYPE: PRT
<213> ORGANISM: Artificial Sequence
<220> FEATURE:
<223> OTHER INFORMATION: Humanized

<400> SEQUENCE: 8

```
Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Thr Gly Ile Val Arg Pro Phe Leu Tyr Trp Gly Gln Gly Thr Leu
            100                 105                 110

Val Thr Val Ser
        115
```

<210> SEQ ID NO 9
<211> LENGTH: 219
<212> TYPE: PRT
<213> ORGANISM: Artificial Sequence
<220> FEATURE:
<223> OTHER INFORMATION: Humanized

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30
```

```
Ser Gly Lys Thr Tyr Leu Tyr Trp Leu Phe Gln Lys Pro Gly Lys Ala
            35                  40                  45

Pro Lys Arg Leu Ile Tyr Leu Val Ser Thr Leu Asp Ser Gly Ile Pro
 50                  55                  60

Ser Arg Phe Ser Gly Ser Gly Ser Gly Thr Glu Phe Thr Leu Thr Ile
 65                  70                  75                  80

Ser Ser Leu Gln Pro Glu Asp Phe Ala Thr Tyr Tyr Cys Leu Gln Gly
                85                  90                  95

Thr His Phe Pro His Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 10
<211> LENGTH: 444
<212> TYPE: PRT
<213> ORGANISM: Artificial Sequence
<220> FEATURE:
<223> OTHER INFORMATION: Humanized

<400> SEQUENCE: 10

Glu Val Pro Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
 50                  55                  60

Lys Gly Arg Phe Thr Ile Ser Arg Asp Asn Ala Lys Ser Ser Leu Tyr
 65                  70                  75                  80

Leu Gln Met Asn Ser Leu Arg Ala Glu Asp Thr Ala Val Tyr Tyr Cys
                85                  90                  95

Thr Thr Gly Ile Val Arg Pro Phe Leu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

Ser Gly Leu Tyr Ser Leu Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
    275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
        340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
        420                 425                 430

Tyr Thr Gln Lys Ser Leu Ser Leu Ser Leu Gly Lys
    435                 440

<210> SEQ ID NO 11
<211> LENGTH: 220
<212> TYPE: PRT
<213> ORGANISM: Artificial Sequence
<220> FEATURE:
<223> OTHER INFORMATION: Humanized

<400> SEQUENCE: 11

Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
            85                  90                  95

```
Thr Thr Gly Ile Val Arg Pro Phe Leu Tyr Trp Gly Gln Gly Thr Leu
            100             105             110

Val Thr Val Ser Ser Ala Ser Thr Lys Gly Pro Ser Val Phe Pro Leu
            115             120             125

Ala Pro Ser Ser Lys Ser Thr Ser Gly Gly Thr Ala Ala Leu Gly Cys
    130             135             140

Leu Val Lys Asp Tyr Phe Pro Glu Pro Val Thr Val Ser Trp Asn Ser
145             150             155             160

Gly Ala Leu Thr Ser Gly Val His Thr Phe Pro Ala Val Leu Gln Ser
                165             170             175

Ser Gly Leu Tyr Ser Leu Ser Ser Val Val Thr Val Pro Ser Ser Ser
            180             185             190

Leu Gly Thr Gln Thr Tyr Ile Cys Asn Val Asn His Lys Pro Ser Asn
            195             200             205

Thr Lys Val Asp Lys Lys Val Glu Pro Lys Ser Cys
210             215             220
```

CELL CULTURE METHODS

CROSS-REFERENCE TO RELATED APPLICATION

This application is the U.S. national stage application of International Patent Application No. PCT/EP2018/064102, filed May 29, 2018.

The Sequence Listing for this application is labeled "Seq-List.txt" which was created on Oct. 28, 2019 and is 11 KB. The entire content of the sequence listing is incorporated herein by reference in its entirety.

FIELD OF THE INVENTION

The present invention belongs to the field of the manufacture of recombinant proteins, particularly antibodies. More specifically, it relates to cell culture methods for expressing proteins with reduced heterogeneity during commercial scale manufacturing.

BACKGROUND OF THE INVENTION

Development of recombinant proteins as therapeutic proteins, such as therapeutic antibodies, requires production of the recombinant proteins at an industrial scale. In order to achieve this, different expression systems, both prokaryotic and eukaryotic systems, may be employed. Over the past two decades, however, the majority of the therapeutic proteins approved as therapeutic have been manufactured through mammalian cell cultures and such system remains the preferred expression system for producing large quantity of recombinant polypeptides for human use.

Mammalian cell cultures, however, present significant challenges. The titer of recombinant protein produced is generally very low compared with other eukaryotic productions systems such as those based on yeast and insect cells.

Over the last 30 years, much effort has been dedicated to establishing the basic parameters of cell culture and recombinant polypeptide expression with much focus of the research dedicated to reaching optimal cell growth through changes of the composition of the cell culture media (see e.g. Hecklau C., et al. J Biotech 218 (2016) 53-63; Zang Li. et al. Anal. Chem 83 (2011) 5422-5430) and operating conditions and, development of large bioreactors.

Whilst yield is still a very important aspect of mammalian cell culture, in recent years, the focus has shifted towards controlling product quality and process consistency at all stages of development and production scale. Therapeutic proteins produced by mammalian cell culture exhibit varying levels of heterogeneity. Such heterogeneity includes, but is not limited to, different glycosylation patterns, differences resulting from deamidation or oxidation, different charge or size variants. Heterogeneity of recombinant proteins may also lead to differences in product colour, e.g. between different batches of the same protein manufactured by the same manufacturing process. Such heterogeneity and in particular, differences in colour of the recombinant protein of interest, becomes more apparent when the therapeutic proteins are formulated at high concentrations. In recent years, there has been a steady trend toward subcutaneous delivery of therapeutic proteins which requires formulating therapeutic proteins at high concentrations. High concentrations have been associated with increased aggregate levels (Purdie J., et al. Biotechnology Progress, 2016, 32, 998-1008). Increased charge variants, such as increased levels of acidic species may affect the protein stability (Banks D. D., et al. Journal of pharmaceutical sciences, 2009, 98, 4501-10) whilst the colour of the concentrated therapeutic protein may be more intense.

Cell culture conditions, such as the composition of the medium (Kshirsagar R., et al. Biotechnology and Bioengineering, 109:10, 2523-2532 (2012); US 2013/0281355; WO 2013/158275) and the growing conditions, including pH and temperature (U.S. Pat. No. 8,765,413) have been shown to impact the quality attributes of therapeutic proteins. Yet, there remains the need to provide further improved cell culture methods for the production of therapeutic proteins, and, in particular, therapeutic antibodies with minimal heterogeneity.

SUMMARY OF THE INVENTION

The present invention addresses the above-identified need by reducing the total amount of cysteine or cystine and tryptophan in the cell culture medium during the production phase of the recombinant proteins.

The following specific embodiments are described as numbered hereinafter:

Embodiment 1

A process for producing a recombinant protein comprising:
a. culturing host cells capable of producing a recombinant protein in a medium;
b. progressing the culture through a production phase wherein the recombinant protein is produced by the cells, wherein, during said production phase, the culture is supplemented with
cysteine or cystine up to a total amount of from 10 wt % to 30 wt % of the expected total amount of recombinant protein produced; and/or
tryptophan up to a total amount of from 8 wt % to 35 wt % of the expected total amount of recombinant protein produced,
c. and, optionally, recovering the recombinant protein from the cell culture medium.

Embodiment 2

The process according to Embodiment 1, wherein the culture is supplemented with cysteine or cystine up to a total amount of from 12 wt % to 28 wt % of the expected total amount of recombinant protein produced, such as a total amount of from 12 wt % to 25 wt %, e.g. from 12 wt % to 20 wt % of the expected total amount of recombinant protein produced.

Embodiment 3

The process according to Embodiment 1 or 2, wherein the culture is supplemented with tryptophan up to a total amount of from 8 wt % to 30 wt % of the expected total amount of recombinant protein produced, such as a total amount of from 8 wt % to 25 wt %, e.g. from 8 wt % to 20 wt % of the expected total amount of recombinant protein produced.

Embodiment 4

The process according to any one of the preceding Embodiments, wherein the total amount of cysteine or cystine provided during the process is from 2.9 to 12 g/($10^{12}$ cells), such as from 2.9 to 7 g/($10^{12}$ cells), e.g. from 5.6 to 7 g/($10^{12}$ cells), wherein cells refers to the expected integral viable cell count at the end of the production phase.

Embodiment 5

The process according to any one of the preceding Embodiments, wherein the total amount of tryptophan provided during the process is from 2.5 to 7 g/($10^{12}$ cells), such as from 2.5 to 3.5 g/($10^{12}$ cells/L), wherein cells refers to the expected integral viable cell count at the end of the production phase.

Embodiment 1a

A process for producing a recombinant protein comprising:
a. culturing host cells capable of producing a recombinant protein in a medium;
b. progressing the culture through a production phase wherein the recombinant protein is produced by the cells, wherein, during said production phase, the culture is supplemented with
   cysteine or cystine up to a total amount of from 10 wt % to 30 wt % of the total amount of recombinant protein produced; and/or
   tryptophan up to a total amount of from 8 wt % to 35 wt % of the total amount of recombinant protein produced,
c. and, optionally, recovering the recombinant protein from the cell culture medium.

Embodiment 2a

The process according to Embodiment 1, wherein the culture is supplemented with cysteine or cystine up to a total amount of from 12 wt % to 28 wt % of the total amount of recombinant protein produced, such as a total amount of from 12 wt % to 25 wt %, e.g. from 12 wt % to 20 wt % of the total amount of recombinant protein produced.

Embodiment 3a

The process according to Embodiment 1 or 2, wherein the culture is supplemented with tryptophan up to a total amount of from 8 wt % to 30 wt % of the total amount of recombinant protein produced, such as a total amount of from 8 wt % to 25 wt %, e.g. from 8 wt % to 20 wt % of the total amount of recombinant protein produced.

Embodiment 4a

The process according to any one of the preceding Embodiments, wherein the total amount of cysteine or cystine provided during the process is from 2.9 to 12 g/($10^{12}$ cells), such as from 2.9 to 7 g/($10^{12}$ cells), e.g. from 5.6 to 7 g/($10^{12}$ cells), wherein cells refers to the integral viable cell count at the end of the production phase.

Embodiment 5a

The process according to any one of the preceding Embodiments, wherein the total amount of tryptophan provided during the process is from 2.5 to 7 g/($10^{12}$ cells), such as from 2.5 to 3.5 g/($10^{12}$ cells/L), wherein cells refers to the integral viable cell count at the end of the production phase.

Embodiment 6

The process according to any one of the preceding Embodiments, wherein the total amount of cysteine or cystine and/or tryptophan in the culture is reached by adding cysteine or cystine and/or tryptophan to the cell culture medium:
a. at the beginning of the production phase,
b. once or multiple times at any time point during the production phase,
c. through continuous addition during the production phase, or
d. in any combination of a., b. and c.

Embodiment 7

The process according to any one of the preceding Embodiments, wherein the process is a batch process, such as a fed-batch process.

Embodiment 8

The process according to any one of the preceding Embodiments, wherein cysteine or cystine and/or tryptophan are provided through daily addition during the production phase.

Embodiment 9

The process according to Embodiment 8, wherein cysteine or cystine is depleted in the culture before cysteine or cystine is added on the next day, e.g. by reducing cysteine or cystine addition to a level between 5.6 and 7 g/($10^{12}$ cells), wherein cells refers to the expected integral viable cell count at the end of the production phase.

Embodiment 9a

The process according to Embodiment 8, wherein cysteine or cystine is depleted in the culture before cysteine or cystine is added on the next day, e.g. by reducing cysteine or cystine addition to a level between 5.6 and 7 g/($10^{12}$ cells), wherein cells refers to the integral viable cell count at the end of the production phase.

Embodiment 10

The process according to Embodiment 8 or 9, wherein during the late
stage of production, i.e. when the cells have already reached the maximum viable cell density, tryptophan is depleted in the culture before tryptophan is added on the next day.

Embodiment 11

The process according to any one of the preceding Embodiments, wherein the cysteine or cystine concentration in the cell culture medium does not exceed 0.9 g/L at any time point during the production phase, preferably wherein the cysteine or cystine concentration in the cell culture medium does not exceed 0.3 g/L at any time point during the production phase.

Embodiment 12

The process according to any one of the preceding Embodiments, wherein the tryptophan concentration in the cell culture medium does not exceed 0.6 g/L at any time point during the production phase, preferably wherein the tryptophan concentration in the cell culture medium does not exceed 0.3 g/L at any time point during the production phase.

Embodiment 13

The process, wherein the production phase is performed for at least 7 days, preferably at least 14 days.

Embodiment 14

The process according to any one of the preceding Embodiments, wherein at any time point during the 2nd half of the production phase:
the amount of cysteine or cystine in the culture is from 10 wt % to 30% of the expected amount of recombinant protein produced; and/or
the amount of tryptophan in the culture is from 8 wt % to 35% of the expected amount of recombinant protein produced.

Embodiment 15

The process according to any one of the preceding Embodiments, wherein at any time point during the production phase:
the amount of cysteine or cystine in the culture is from 10 wt % to 30% of the expected amount of recombinant protein produced; and/or
the amount of tryptophan in the culture is from 8 wt % to 35% of the expected amount of recombinant protein produced.

Embodiment 14a

The process according to any one of the preceding Embodiments, wherein at any time point during the 2nd half of the production phase:
the amount of cysteine or cystine in the culture is from 10 wt % to 30% of the amount of recombinant protein produced; and/or
the amount of tryptophan in the culture is from 8 wt % to 35% of the amount of recombinant protein produced.

Embodiment 15a

The process according to any one of the preceding Embodiments, wherein at any time point during the production phase:
the amount of cysteine or cystine in the culture is from 10 wt % to 30% of the amount of recombinant protein produced; and/or
the amount of tryptophan in the culture is from 8 wt % to 35% of the amount of recombinant protein produced.

Embodiment 16

The process according to any one of the preceding Embodiments, wherein the host cells are mammalian cells, preferably CHO cells.

Embodiment 17

The process according to any one of the preceding Embodiments, wherein the recombinant protein is an antibody or an antigen-binding fragment thereof.

Embodiment 18

The process according to Embodiment 17, wherein the antibody or antigen-binding fragment thereof is:
1) an antibody or antigen-binding fragment thereof which
   a. comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or
   b. comprises a light variable region having the sequence as defined in SEQ ID NO: 7 and a heavy variable region having the sequence as defined in SEQ ID NO: 8; or
   c. comprises a light variable region having at least 80% identity or similarity, preferably 90% identity or similarity to the sequence as defined in SEQ ID NO: 7 and a heavy variable region having at least 80% identity or similarity, preferably 90% identity or similarity to the sequence as defined in SEQ ID NO: 8;
   d. comprises a light variable region having the sequence as defined in SEQ ID NO: 7 and a heavy chain having the sequence as defined in SEQ ID NO: 11; or
   e. comprises a light variable region having at least 80% identity or similarity, preferably 90% identity or similarity to the sequence as defined in SEQ ID NO: 7 and a heavy chain having at least 80% identity or similarity, preferably 90% identity or similarity to the sequence as defined in SEQ ID NO: 11; or
2) an antibody which comprises a light chain having the sequence as defined in SEQ ID NO: 9 and a heavy chain having the sequence as defined in SEQ ID NO: 10; or
3) an antibody which comprises a light chain having at least 80% identity or similarity, preferably 90% identity or similarity to the sequence as defined in SEQ ID NO: 9 and a heavy chain having at least 80% identity or similarity, preferably 90% identity or similarity to the sequence as defined in SEQ ID NO: 10.

Embodiment 19

The process according to any one of the preceding Embodiments, wherein the production phase is carried out in a bioreactor, preferably with a volume of equal or more than 50 L, equal or more than 100 L, equal or more than 500 L, equal or more than 1000 L, equal or more than 2,000 L, equal or more than 5,000 L, equal or more than 10,000 L or equal or more than 20,000 L.

Embodiment 20

The process according to any one of the preceding Embodiments, wherein the process comprises the step of recovering the recombinant protein from the cell culture medium and a further step of purifying the recombinant protein.

Embodiment 21

The process according to Embodiment 20, wherein the purification comprises Protein A chromatography.

Embodiment 22

The process according to Embodiment 20 or 21, further comprising the step of formulating the purified recombinant protein.

Embodiment 23

The process according to Embodiment 22, wherein the recombinant protein is formulated in a liquid formulation comprising one or more amino acids and a surfactant.

Embodiment 24

The process according to Embodiment 23, wherein the formulation comprises histidine and/or proline.

Embodiment 25

The process according to Embodiment 24, wherein the formulation comprises histidine in a concentration of 5 mM to 100 mM, e.g. a concentration of 10 mM to 50 mM, and/or proline in a concentration of 100 mM to 500 mM, at a pH between 5 and 7.4, such as between 5 and 6.5, e.g. between 5 and 6.

Embodiment 26

The process according to Embodiment 25, wherein the formulation comprises histidine in a concentration of 30 mM and proline in a concentration of 250 mM, at a pH between 5.2 and 6.0, preferably about 5.6.

Embodiment 27

The process according to any one of Embodiments 23 to 26, wherein the surfactant is polysorbate 80, preferably in a concentration of 0.001% to 0.1% (w/v), e.g. 0.005% to 0.1%, such as 0.01% to 0.1%, e.g. 0.01% to 0.05%, such as 0.03%.

Embodiment 28

The processing according to any one of Embodiments 23 to 27, wherein the recombinant protein is an antibody and the antibody is formulated at a concentration of 10 mg/ml to 250 mg/ml, e.g. 20 mg/ml to 250 mg/ml, such as 50 mg/ml to 250 mg/ml, e.g. 120 mg/ml to 160 mg/ml, such as about 140 mg/ml.

Embodiment 29

The process according to any one of the preceding Embodiments, wherein the process reduces the heterogeneity of the recombinant proteins produced, wherein said reduction of heterogeneity comprises reducing:
a. charge heterogeneity, preferably acidic peak group (APG); and/or
b. amino acid oxidation, isomerization, fragmentation, other covalent adducts glycation, deamidation, cysteinylation; and/or
c. colour or intensity of colour, e.g. between different batches of the recombinant protein; and/or
d. high molecular weight species (HMWS); and/or
e. recombinant protein instability.

Embodiment 30

A process for producing a recombinant protein comprising:
a. culturing host cells capable of producing a recombinant protein in a medium;
b. progressing the culture through a production phase wherein the recombinant protein is produced by the cells and the cell culture medium is supplemented with cysteine or cystine and/or tryptophan, wherein
   the total amount of cysteine or cystine provided during the process is from 2.9 to 7 g/($10^{12}$ cells), e.g. from 5.6 to 7 g/($10^{12}$ cells), wherein cells refers to the expected integral viable cell count at the end of the production phase, and/or
   the total amount of tryptophan provided during the process is from 2.5 to 3.5 g/($10^{12}$ cells), wherein cells refers to the expected integral viable cell count at the end of the production phase,
c. and, optionally, recovering the recombinant protein from the cell culture medium.

Embodiment 30a

A process for producing a recombinant protein comprising:
a. culturing host cells capable of producing a recombinant protein in a medium;
b. progressing the culture through a production phase wherein the recombinant protein is produced by the cells and the cell culture medium is supplemented with cysteine or cystine and/or tryptophan, wherein
   the total amount of cysteine or cystine provided during the process is from 2.9 to 7 g/($10^{12}$ cells), e.g. from 5.6 to 7 g/($10^{12}$ cells), wherein cells refers to the integral viable cell count at the end of the production phase, and/or
   the total amount of tryptophan provided during the process is from 2.5 to 3.5 g/($10^{12}$ cells), wherein cells refers to the integral viable cell count at the end of the production phase,
c. and, optionally, recovering the recombinant protein from the cell culture medium.

Embodiment 31

The process according to Embodiment 30, wherein the process has one or more of the further features recited in any one of Embodiments 2 to 29.

Embodiment 32

A method for reducing the heterogeneity of the population of recombinant proteins in a batch produced in production phase by recombinant host cells comprising limiting the total amount of
a. cysteine or cystine and/or
b. tryptophan
present in the cell culture medium during the production phase of the recombinant protein.

Embodiment 33

The method according to Embodiment 32, wherein the process has one or more of the further features recited in any one of Embodiments 2 to 29.

Embodiment 34

A recombinant protein preparation obtainable or obtained by the process according to any one of the preceding Embodiments.

Embodiment 35

A pharmaceutical composition comprising an antibody, wherein the composition has one or more of the further features recited in any one of Embodiments 23 to 28, preferably wherein the antibody is the antibody recited in Embodiment 18.

BRIEF DESCRIPTION OF THE DRAWINGS

FIGS. 1A-1C: Description of the computational analysis to measure the total amount of amino acids cysteine or cystine and tryptophan added throughout the production phase carried out in a bioreactor (FIG. 1A) per weight percentage of the recombinant protein produced (FIG. 1B) resulting in the ratio (FIG. 1C).

FIGS. 2A-2D: Impact of total quantity added of tryptophan and cysteine or cystine wt % (g/g) of total mAb1 produced on b* value normalized to 40 mg/mL (FIG. 2A) and_acidic peak group (APG) variant (FIG. 2B), respectively. The maximum tryptophan and cysteine or cystine concentrations do not impact the b* value (FIG. 2C) or the APG % (FIG. 2D).

FIGS. 11A-11C: Contour plot of the impact of total amount of cysteine or cystine and tryptophan added to the cell culture medium during production phase per IVCC*10$^{-12}$ at end of production phase on IVCC for 14 days production is shown in FIG. 11A. Contour plot showing the impact of total amount of cysteine or cystine and tryptophan added to the cell culture medium during production phase per IVCC*10$^{-12}$ at end of production phase on final mAb HPLC titer is shown in FIG. 11B. Description of the computational analysis to measure the amount of amino acids cysteine or cystine and tryptophan added throughout the production phase carried out in a bioreactor per IVCC*10$^{-12}$ at end of production phase is shown in FIG. 11C FIG. 12: Contour plot of the impact of maximum concentrations of cysteine or cystine and tryptophan reached in the cell culture medium throughout the production phase on IVCC normalized to the CSV.

FIG. 15B on APG variant for mAb3 and FIG. 15C on APG, BPG (Basic Peak Group) and main group variants for mAb4.

In FIG. 16A, the APG variant of mAb1, mAb2, mAb3 and mAb4 was plotted against the total cysteine or cystine quantity added wt % of total recombinant mAb1, mAb2, mAb3 and mAb4 produced by weight. In FIG. 16B, a multiple linear regression model of the APG variant of the recombinant monoclonal antibody mAb1, mAb2 and mAb3 and the recombinant multispecific antibody, mAb4, was plotted as a function of cysteine or cystine and tryptophan total quantity added wt % of total recombinant mAb produced by weight.

DETAILED DESCRIPTION OF THE INVENTION

Figure 3A:
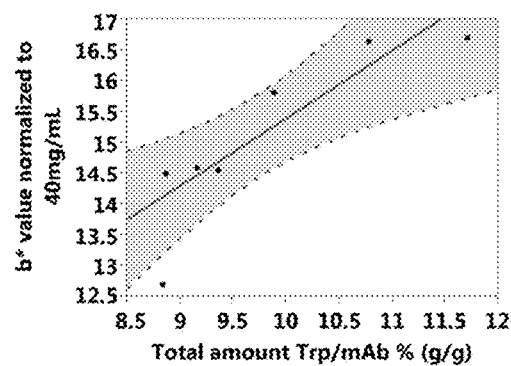
FIGS. 3A-3D: Impact of total quantity added of tryptophan and cysteine or cystine wt % of total mAb1 weight produced (g/g) on- b* value normalized to 40 mg/mL FIG. 3A) acidic peak group (APG) variant (FIG. 3B), respectively and lack of correlation for maximum concentrations of cysteine or cystine (FIG. 3C) and tryptophan (FIG. 3D) on APG.

The invention is based on the finding that by limiting the total amount of cysteine or cystine and/or tryptophan used in the cell culture medium during the production phase in a process for manufacturing a recombinant protein, the heterogeneity of the recombinant proteins produced is reduced. Hence, the present invention teaches the use of a limited amount of cysteine or cystine and/or tryptophan in the cell culture medium for reducing the heterogeneity of an antibody or antigen-binding fragment thereof expressed in the medium.

The reduced heterogeneity is preferably with respect to:
a. charge, preferably acidic peak group (APG) heterogeneity; and/or
b. amino acid oxidation, isomerization, fragmentation, other covalent adducts glycation, deamidation, cysteinylation; and/or
c. colour or intensity of colour (b*value normalised to 40 mg/mL); and/or
d. high molecular weight species (HMWS) formation; and/or
e. recombinant protein instability and/or
f. combinations thereof.

The term "heterogeneity" as used herein refers to differences between individual molecules, e.g. recombinant proteins, in a population of molecules produced by the same manufacturing process, or within the same manufacturing batch. Heterogeneity can result from incomplete or inhomogeneous modifications of the recombinant proteins, e.g. due to post-translational modifications of the expressed protein. Such modifications can be the result of deamination reactions and/or oxidation reactions and/or covalent addition of small molecules such as glycation reactions and/or isomerization reactions and/or fragmentation reactions and/or other reactions and also include variation on the glycation patterns. The chemo-physical manifestation of such heterogeneity leads to various characteristics in the resulting recombinant protein preparations which include, but are not limited to, charge variant profile, colour or colour intensity and molecular weight profile.

The term "production phase" according to the present invention comprises that stage of cell culturing during the process for manufacturing a recombinant protein when the cells express (i.e. produce) the recombinant protein(s). The production phase begins when the titer of the desired product is increased and ends with harvest of the cells or the cell culture fluid or supernatant. Typically, at the beginning of the production phase, the cell culture is transferred to a bioreactor. Harvest is the step during which the cell culture fluid is removed from the e.g. production vessel, in order for the recombinant protein e.g. the recombinant antibody, to be recovered and purified in subsequent steps. The term "initial cell culture weight" when used herein refers to the weight of the culture at the start of the production phase, typically the weight upon inoculation of the bioreactor.

In a first aspect, the invention provides for a process for producing a recombinant protein comprising:
a. culturing host cells capable of producing a recombinant protein in a medium;
b. progressing the culture through a production phase wherein the recombinant protein is produced by the cells, wherein, during said production phase, the culture is supplemented with
  a. cysteine or cystine up to a total amount of from 10 wt % to 30 wt % of the expected total amount of recombinant protein produced; and/or
  b. tryptophan up to a total amount of from 8 wt % to 35 wt % of the expected total amount of recombinant protein produced,
and, optionally, recovering the recombinant protein from the cell culture medium.

As it will be apparent from the description of the invention hereinafter, the culture is supplemented with cysteine or cystine and/or tryptophan; such supplementation may be performed with:
1. cysteine; or
2. cystine; or
3. cysteine and cystine; or
4. cysteine and tryptophan; or
5. cystine and tryptophan; or
6. cysteine, cystine and tryptophan; or
7. tryptophan.

When used herein, the expressions "total amount of cysteine or cystine" or "cysteine or cystine up to a total amount." refer to a) the total amount of cysteine alone if no cystine is used for the process, b) the total amount of cystine alone if no cysteine used for the process or c) the total amount of cysteine+cystine if both compounds are used for the process. Cysteine and cystine in the cell culture medium are in constant equilibrium wherein two molecules of cysteine oxidize into a molecule of cystine and reduce back to two molecules of cysteine.

The total amount of cysteine or cystine and/or tryptophan may be expressed herein as a percentage of the total amount of recombinant protein produced. The term "wt %" as used herein refers to percentage of weight. "Total" refers to the total amount as determined at the end of the production phase, i.e. the total amount of cysteine or cystine and/or tryptophan added over the course of the production phase and the total amount of recombinant protein produced over the course of the production phase, wherein the total amount of recombinant protein produced is measured at the end of the production phase.

FIGS. 1A-1C show how the total amount of cysteine or cystine and/or tryptophan per wt % of recombinant protein produced is calculated. The total amount of cysteine or cystine or tryptophan added is calculated as a function of the feed rate (or feed volume) and the concentration of cysteine or cystine or tryptophan in that feed and the concentration of cysteine or cystine or tryptophan in the medium where the feed is added per volume of feed added (FIG. 1A). The quantity of recombinant protein produced is calculated as a function of the final volume of the cell culture medium and the final recombinant protein titer (FIG. 1B) The ratio of these two calculated parameters is the total amount of cysteine or cystine and/or tryptophan added per quantity of recombinant protein produced (F.

The host cells may initially (in step a.) be grown in a cell culture medium which may or may not already include cysteine or cystine and tryptophan. If the cell culture medium already includes an initial amount of cysteine or cystine and/or tryptophan, then the total amount will include this initial amount.

In one embodiment of the process of the invention, the culture is supplemented with cysteine or cystine up to a total amount of from 12.06 wt % to 28.03 wt % of the expected total amount of recombinant protein produced, such as a total amount of from 12 wt % to 28 wt %, e.g. from 12 wt % to 25 wt %, such as from 12 wt % to 20 wt % of the expected total amount of recombinant protein produced.

In another embodiment of the process of the invention, wherein the culture is supplemented with tryptophan up to a total amount of from 8.84 wt % to 32.06 wt % of the expected total amount of recombinant protein produced, such as a total amount of from 8 wt % to 30 wt %, e.g. from 8 wt % to 25 wt %, such as from 8 wt % to 20 wt % of the expected total amount of recombinant protein produced.

Alternatively, the total amount of cysteine or cystine and/or tryptophan may be expressed as the total amount added during the process relative to the integral viable cell count at the end of the production phase. In one embodiment, the total amount of cysteine and/or cystine provided during the process is from 2.9 to 12 g/($10^{12}$ cells), such as from 2.9 to 7 g/($10^{12}$ cells), e.g. from 5.6 to 7 g/($10^{12}$ cells), wherein cells refers to the expected integral viable cell count at the end of the production phase. In another embodiment, the total amount of tryptophan provided during the process is from 2.5 to 7 g/($10^{12}$ cells), such as from 2.5 to 3.5 g/($10^{12}$ cells/L), wherein cells refers to the expected integral viable cell count at the end of the production phase.

It should be understood that the skilled person would know how to measure the amount of cysteine or cystine and/or tryptophan added to and/or present in a cell culture at a specific phase, such as the production phase. For example, this can be done as described in the Examples herein. Similarly, the skilled person would know how to measure the total amount of recombinant protein produced by a cell culture and consequently apply the teaching of the present invention to achieve the desired technical effect. For example, this can be done as described in the Examples herein, such as using a ForteBio Octet model analyser (ForteBio, Inc., Menlo Park, Calif.) or protein A high-pressure liquid chromatography (HPLC) with cell culture supernatant samples which were stored at −80° C. prior to analysis.

In order to design a process according to the invention, wherein the amounts of cysteine or cystine and/or tryptophan per expected total amount of recombinant protein produced are kept within certain ranges, it may be required to perform one or more initial experiments to determine the approximate levels of recombinant protein produced by particular host cells under particular culturing conditions. Once the approximate total levels of recombinant protein produced are known, a process according to the invention can be designed wherein the amounts of cysteine or cystine and/or tryptophan per expected total amount of recombinant protein produced are kept within the specified ranges.

Various strategies may be employed for reaching the total amount of cysteine or cystine and/or tryptophan in the cell culture medium during the production phase. In one embodiment, the total amount may be reached by adding cysteine or cystine and/or tryptophan right at the beginning of the production phase, for example only once or as being already included in the production cell culture medium. In another embodiment, the total amount may be reached by the summation of additions, for example daily addition or continuous addition, during the production phase. In yet another embodiment, the total amount may be reached by a combination of the initial cysteine/cysteine and/or tryptophan concentration in the cell culture fluid at the start of the production phase, and by way of additions.

Accordingly, in one embodiment of the process of the invention, the total amount of cysteine or cystine and/or tryptophan in the cell culture medium is reached by adding cysteine or cystine and/or tryptophan to the cell culture medium:
　a. at the beginning of the production phase,
　b. once or multiple times at any time point during the production phase,
　c. through continuous addition during the production phase, or
　d. in any combination of a., b. and c.

In a preferred embodiment, the cysteine or cystine and/or tryptophan are added at the beginning of the production phase and are added through daily bolus additions during the production phase. Preferably the production phase lasts at least for 7 days, more preferably for more than 7 days, such as 10 days, more preferably for 14 or more days.

In a preferred embodiment, the cysteine or cystine concentration in the cell culture medium does not exceed 0.9 g/L at any time point during the production phase, preferably the cysteine or cystine concentration in the cell culture medium does not exceed 0.3 g/L at any time point during the production phase.

Furthermore, in a preferred embodiment, the tryptophan concentration in the cell culture medium does not exceed 0.6 g/L at any time point during the production phase, preferably the tryptophan concentration in the cell culture medium does not exceed 0.3 g/L at any time point during the production phase.

In one embodiment, cysteine or cystine are added daily to the cell culture medium, and at day 6 the cysteine or cystine in the cell culture medium increases a maximum concentration of 0.3 g/L, and from day 7 to 14 the cysteine or cystine in the cell culture medium increases to a maximum concentration of 0.9 g/L.

In some embodiments, the amounts of cysteine or cystine and/or tryptophan are not only within the specified ranges when calculated over the entire production phase at the end of the production phase, but also at any time point during parts of the production phase or even at any time point during the entire production phase. Thus, in one embodiment, at any time point during the $2^{nd}$ half of the production phase (e.g. day 7 to 14 of a 14-day production phase):
　the amount of cysteine or cystine in the culture is from 10 wt % to 30% of the expected amount of recombinant protein produced; and/or
　the amount of tryptophan in the culture is from 8 wt % to 35% of the expected amount of recombinant protein produced.

In another embodiment, at any time point during the production phase:
　the amount of cysteine or cystine in the culture is from 10 wt % to 30% of the expected amount of recombinant protein produced; and/or
　the amount of tryptophan in the culture is from 8 wt % to 35% of the expected amount of recombinant protein produced.

When cysteine or cystine is provided to the cells through daily additions, the cysteine or cystine may be depleted in the culture before the next daily addition is provided. In one embodiment, cysteine or cystine is depleted in the culture before cysteine or cystine is added on the next day, e.g. by reducing cysteine or cystine addition to a level between 5.6 and 7 g/[$10^{12}$ cells]. In a second embodiment, tryptophan is depleted in the culture during cell culturing during the late stage of production, i.e. when the cells already reached the maximum viable cell density, e.g. beginning depletion at day 8 or later in a 14-day production phase.

Without wishing to be bound by theory, it is believed that, despite the cysteine or cystine are being depleted, the cells in the production phase do no remain deprived of cysteine or cystine but are hypothesized to possess an internal mechanism aimed at storing the cysteine or cystine made available in the cell culture medium, through addition, as an inactive metabolite, which can be converted to cysteine or cystine once depletion occur.

In a further independent aspect, the invention relates to a process for producing a recombinant protein comprising:
a. culturing host cells capable of producing a recombinant protein in a medium;
b. progressing the culture through a production phase wherein the recombinant protein is produced by the cells and the cell culture medium is supplemented with cysteine or cystine and/or tryptophan, wherein
the total amount of cysteine or cystine provided during the process is from 2.9 to 7 g/($10^{12}$ cells), e.g. from 5.6 to 7 g/($10^{12}$ cells), wherein cells refers to the expected integral viable cell count at the end of the production phase, and/or
the total amount of tryptophan provided during the process is from 2.5 to 3.5 g/($10^{12}$ cells), wherein cells refers to the expected integral viable cell count at the end of the production phase,
c. and, optionally, recovering the recombinant protein from the cell culture medium.

In one embodiment of this process, the cell culture medium is supplemented with cysteine or cystine up to a total amount of from 12 wt % to 28 wt % of the expected total amount of recombinant protein produced, such as a total amount of from 12 wt % to 25 wt %, e.g. from 12 wt % to 20 wt % of the expected total amount of recombinant protein produced.

In another embodiment of this process, the cell culture medium is supplemented with tryptophan up to a total amount of from 8 wt % to 30 wt % of the expected total amount of recombinant protein produced, such as a total amount of from 8 wt % to 25 wt %, e.g. from 8 wt % to 20 wt % of the expected total amount of recombinant protein produced.

In another embodiment of this process, the total amount of cysteine or cystine and/or tryptophan in the cell culture medium is reached by adding cysteine or cystine and/or tryptophan to the cell culture medium:
a. at the beginning of the production phase,
b. once or multiple times at any time point during the production phase,
c. through continuous addition during the production phase, or
d. in any combination of a., b. and c.

In another embodiment of this process, the process is a batch process, such as a fed-batch process. In another embodiment of this process, the cysteine or cystine and/or tryptophan are provided through daily addition during the production phase.

In another embodiment of this process, cysteine or cystine is depleted in the cell culture medium before cysteine or cystine is added on the next day, e.g. by reducing cysteine or cystine addition to a level between 5.6 and 7 g/[$10^{12}$ cells].

In another embodiment of this process, during the late stage of production, i.e. when the cells have already reached the maximum viable cell density, tryptophan is depleted in the cell culture medium before tryptophan is added on the next day.

In another embodiment of this process, the cysteine or cystine concentration in the cell culture does not exceed 0.9 g/L at any time point during the production phase, preferably wherein the cysteine or cystine concentration in the cell culture does not exceed 0.3 g/L at any time point during the production phase.

In another embodiment of this process, the tryptophan concentration in the cell culture does not exceed 0.6 g/L at any time point during the production phase, preferably wherein the tryptophan concentration in the cell culture does not exceed 0.3 g/L at any time point during the production phase.

In another embodiment of this process, the production phase is performed for at least 7 days, preferably at least 14 days.

In one embodiment of this process, at any time point during the $2^{nd}$ half of the production phase:
a. the amount of cysteine or cystine in the cell culture medium is from 10 wt % to 30% of the expected amount of recombinant protein produced; and/or
b. the amount of tryptophan in the cell culture medium is from 8 wt % to 35% of the expected amount of recombinant protein produced.

In another embodiment of this process, at any time point during the production phase:
a. the amount of cysteine or cystine is from 10 wt % to 30% of the expected amount of recombinant protein produced; and/or
b. the amount of tryptophan is from 8 wt % to 35% of the expected amount of recombinant protein produced.

In another embodiment of this process, the host cells are mammalian cells, preferably CHO cells.

In another embodiment of this process, the recombinant protein is an antibody or an antigen-binding fragment thereof.

In another embodiment of this process, the production phase is carried out in a bioreactor, preferably with a volume of equal or more than 50 L, equal or more than 100 L, equal or more than 500 L, equal or more than 1000 L, equal or more than 2,000 L, equal or more than 5,000 L, equal or more than 10,000 L or equal or more than 20,000 L.

In one embodiment of this process, the process comprises the step of recovering the recombinant protein from the cell culture medium and a further step of purifying the recombinant protein.

In a further embodiment of this process, the purification comprises Protein A chromatography.

In a further embodiment of this process, the process comprises a further the step of formulating the purified recombinant protein.

In one embodiment of this process, the recombinant protein is formulated in a liquid formulation comprising one or more amino acids and a surfactant.

In a further embodiment of this process, the formulation comprises histidine and/or proline.

In an even further embodiment of this process, the formulation comprises histidine in a concentration of 5 mM to 100 mM, e.g. a concentration of 10 mM to 50 mM, and/or proline in a concentration of 100 mM to 500 mM, at a pH between 5 and 7.4, such as between 5 and 6.5, e.g.
between 5 and 6, such as between 5.5 and 6.

In an even further embodiment of this process, the formulation comprises histidine in a concentration of 30 mM and proline in a concentration of 250 mM, at a pH between 5.2 and 6.0, such as about 5.6.

In further embodiment of this process, the surfactant is polysorbate 80, preferably in a concentration of 0.001% to 0.1% (w/v), e.g. 0.005% to 0.1%, such as 0.01% to 0.1%, e.g. 0.01% to 0.05%, such as 0.03%.

In an even further embodiment of this process, the recombinant protein is an antibody and the antibody is formulated at a concentration of 10 mg/ml to 250 mg/ml, e.g. 20 mg/ml to 250 mg/ml, such as 50 mg/ml to 250 mg/ml, e.g. 120 mg/ml to 160 mg/ml, such as about 140 mg/ml.

In another embodiment of this process, the process reduces the heterogeneity of the recombinant proteins produced, wherein said reduction of heterogeneity comprises reducing:
a. charge heterogeneity, preferably acidic peak group (APG); and/or
b. amino acid oxidation, isomerization, fragmentation, other covalent adducts glycation, deamidation, cysteinylation; and/or
c. colour or intensity of colour, e.g. between different batches of the recombinant protein; and/or
d. high molecular weight species (HMWS); and/or
e. recombinant protein instability.

In a further independent aspect, the invention relates to a method for reducing the heterogeneity of the population of recombinant proteins in a batch produced in production phase by recombinant host cells comprising limiting the total amount of
a. cysteine or cystine and/or
b. tryptophan
present in the cell culture medium during the production phase of the recombinant protein.

In one embodiment, the method comprises:
a. culturing host cells capable of producing a recombinant protein in a medium;
b. progressing the culture through a production phase wherein the recombinant protein is produced by the cells, wherein, during said production phase, the culture is supplemented with
cysteine or cystine up to a total amount of from 10 wt % to 30 wt % of the expected total amount of recombinant protein produced; and/or
tryptophan up to a total amount of from 8 wt % to 35 wt % of the expected total amount of recombinant protein produced,
c. and, optionally, recovering the recombinant protein from the cell culture medium.

In one embodiment of the method, the culture is supplemented with cysteine or cystine up to a total amount of from 12 wt % to 28 wt % of the expected total amount of recombinant protein produced, such as a total amount of from 12 wt % to 25 wt %, e.g. from 12 wt % to 20 wt % of the expected total amount of recombinant protein produced.

In another embodiment of the method, the culture is supplemented with tryptophan up to a total amount of from 8 wt % to 30 wt % of the expected total amount of recombinant protein produced, such as a total amount of from 8 wt % to 25 wt %, e.g. from 8 wt % to 20 wt % of the expected total amount of recombinant protein produced.

In another embodiment of the method, the total amount of cysteine or cystine provided during the process is from 2.9 to 12 g/($10^{12}$ cells), such as from 2.9 to 7 g/($10^{12}$ cells), e.g. from 5.6 to 7 g/($10^{12}$ cells), wherein cells refers to the expected integral viable cell count at the end of the production phase.

In another embodiment of the method, the total amount of tryptophan provided during the process is from 2.5 to 7 g/($10^{12}$ cells), such as from 2.5 to 3.5 g/($10^{12}$ cells/L), wherein cells refers to the expected integral viable cell count at the end of the production phase.

In another embodiment of the method, the total amount of cysteine or cystine and/or tryptophan in the cell culture medium is reached by adding cysteine or cystine and/or tryptophan to the cell culture medium:
a. at the beginning of the production phase,
b. once or multiple times at any time point during the production phase,
c. through continuous addition during the production phase, or
d. in any combination of a., b. and c.

In another embodiment of the method, the process is a batch process, such as a fed-batch process.

In another embodiment of the method, cysteine or cystine and/or tryptophan are provided through daily addition during the production phase.

In another embodiment of the method, cysteine or cystine is depleted in the cell culture medium before cysteine or cystine is added on the next day, e.g. by reducing cysteine or cystine addition to a level between 5.6 and 7 g/[$10^{12}$ cells].

In another embodiment of the method, during the late stage of production, i.e. when the cells have already reached the maximum viable cell density, tryptophan is depleted in the cell culture medium before tryptophan is added on the next day.

In another embodiment of the method, the cysteine or cystine concentration in the cell culture medium does not exceed 0.9 g/L at any time point during the production phase, preferably wherein the cysteine or cystine concentration in the cell culture medium does not exceed 0.3 g/L at any time point during the production phase.

In another embodiment of the method, the tryptophan concentration in the cell culture medium does not exceed 0.6 g/L at any time point during the production phase, preferably wherein the tryptophan concentration in the cell culture medium does not exceed 0.3 g/L at any time point during the production phase.

In another embodiment of the method, the production phase is performed for at least 7 days, preferably at least 14 days.

In another embodiment of the method, at any time point during the $2^{nd}$ half of the production phase:
the amount of cysteine or cystine in the culture is from 10 wt % to 30% of the expected amount of recombinant protein produced; and/or
the amount of tryptophan in the culture is from 8 wt % to 35% of the expected amount of recombinant protein produced.

In another embodiment of the method, at any time point during the production phase:
the amount of cysteine or cystine in the culture is from 10 wt % to 30% of the expected amount of recombinant protein produced; and/or
the amount of tryptophan in the culture is from 8 wt % to 35% of the expected amount of recombinant protein produced.

In another embodiment of the method, the host cells are mammalian cells, preferably CHO cells.

In another embodiment of the method, the recombinant protein is an antibody or an antigen-binding fragment thereof.

In another embodiment of the method, the production phase is carried out in a bioreactor, preferably with a volume of equal or more than 50 L, equal or more than 100 L, equal or more than 500 L, equal or more than 1000 L, equal or more than 2,000 L, equal or more than 5,000 L, equal or more than 10,000 L or equal or more than 20,000 L.

In one embodiment of this method, the method comprises the step of recovering the recombinant protein from the cell culture medium and a further step of purifying the recombinant protein.

In a further embodiment of this method, the purification comprises Protein A chromatography.

In a further embodiment of this method, the method comprises a further the step of formulating the purified recombinant protein.

In one embodiment of this method, the recombinant protein is formulated in a liquid formulation comprising one or more amino acids and a surfactant.

In a further embodiment of this method, the formulation comprises histidine and/or proline.

In an even further embodiment of this method, the formulation comprises histidine in a concentration of 5 mM to 100 mM, e.g. a concentration of 10 mM to 50 mM, and/or proline in a concentration of 100 mM to 500 mM, at a pH between 5 and 7.4, such as between 5 and 6.5, e.g. between 5 and 6, such as between 5.5 and 6.

In an even further embodiment of this method, the formulation comprises histidine in a concentration of 30 mM and proline in a concentration of 250 mM, at a pH between 5.2 and 6.0, such as about 5.6.

In further embodiment of this method, the surfactant is polysorbate 80, preferably in a concentration of 0.001% to 0.1% (w/v), e.g. 0.005% to 0.1%, such as 0.01% to 0.1%, e.g. 0.01% to 0.05%, such as 0.03%.

In an even further embodiment of this method, the recombinant protein is an antibody and the antibody is formulated at a concentration of 10 mg/ml to 250 mg/ml, e.g. 20 mg/ml to 250 mg/ml, such as 50 mg/ml to 250 mg/ml, e.g. 120 mg/ml to 160 mg/ml, such as about 140 mg/ml.

In another embodiment of the method, the method reduces the heterogeneity of the recombinant proteins produced, wherein said reduction of heterogeneity comprises reducing:
  a. charge heterogeneity, preferably acidic peak group (APG); and/or
  b. amino acid oxidation, isomerization, fragmentation, other covalent adducts glycation, deamidation, cysteinylation; and/or
  c. colour or intensity of colour, e.g. between different batches of the recombinant protein; and/or
  d. high molecular weight species (HMWS); and/or
  e. recombinant protein instability.

In a further aspect, the invention relates to a recombinant protein preparation obtainable or obtained by the process according to the invention. In one embodiment, the preparation is a bulk preparation. In other embodiments, e.g. when the process comprises further steps of formulating the protein product, the preparation that is obtained is a formulated protein preparation, e.g. a preparation suitable for administration to a patient.

The recombinant proteins, preferably the antibodies or antigen-binding fragments thereof in said preparation so obtained exhibit reduced heterogeneity with respect to the same recombinant proteins obtained with the same process but where the total amount of cysteine or cystine and/or tryptophan during the production phase is not limited as described in the present invention.

In an even further aspect, the invention relates to a pharmaceutical composition comprising an antibody, wherein the composition is a liquid formulation composition one or more amino acids and a surfactant.

In one embodiment, the pharmaceutical composition comprises histidine and/or proline.

In a further embodiment, the pharmaceutical composition comprises histidine and/or proline.

In a further embodiment, the pharmaceutical composition comprises histidine in a concentration of 5 mM to 100 mM, e.g. a concentration of 10 mM to 50 mM, and/or proline in a concentration of 100 mM to 500 mM, at a pH between 5 and 7.4, such as between 5 and 6.5, e.g. between 5 and 6, such as between 5.5 and 6.

In a further embodiment, the pharmaceutical composition comprises histidine in a concentration of 30 mM and proline in a concentration of 250 mM, at a pH between 5.2 and 6.0, such as about 5.6.

In a further embodiment of the pharmaceutical composition, the surfactant is polysorbate 80, preferably in a concentration of 0.001% to 0.1% (w/v), e.g. 0.005% to 0.1%, such as 0.01% to 0.1%, e.g. 0.01% to 0.05%, such as 0.03%.

In a further embodiment of the pharmaceutical composition, the antibody is formulated at a concentration of 10 mg/ml to 250 mg/ml, e.g. 20 mg/ml to 250 mg/ml, such as 50 mg/ml to 250 mg/ml, e.g. 120 mg/ml to 160 mg/ml, such as about 140 mg/ml.

In a further embodiment of the pharmaceutical composition, the antibody is
  1) an antibody or antigen-binding fragment thereof which
    a. comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or
    b. comprises a light variable region having the sequence as defined in SEQ ID NO: 7 and a heavy variable region having the sequence as defined in SEQ ID NO: 8; or
    c. comprises a light variable region having at least 80% identity or similarity, preferably 90% identity or similarity to the sequence as defined in SEQ ID NO: 7 and a heavy variable region having at least 80% identity or similarity, preferably 90% identity or similarity to the sequence as defined in SEQ ID NO: 8;
    d. comprises a light variable region having the sequence as defined in SEQ ID NO: 7 and a heavy chain having the sequence as defined in SEQ ID NO: 11; or
    e. comprises a light variable region having at least 80% identity or similarity, preferably 90% identity or similarity to the sequence as defined in SEQ ID NO: 7 and a heavy chain having at least 80% identity or similarity, preferably 90% identity or similarity to the sequence as defined in SEQ ID NO: 11; or 2) an antibody which comprises a light chain having the sequence as defined in SEQ ID NO: 9 and a heavy chain having the sequence as defined in SEQ ID NO: 10; or
3) an antibody which comprises a light chain having at least 80% identity or similarity, preferably 90% identity or similarity to the sequence as defined in SEQ ID NO: 9 and a heavy chain having at least 80% identity or similarity, preferably 90% identity or similarity to the sequence as defined in SEQ ID NO: 10.

Host Cells and Culture Conditions

The recombinant protein, antibody or antigen-binding fragment thereof may preferably be produced by culturing mammalian host cells, most preferably Chinese Hamster Ovary (CHO) cells.

The term "cell culture" or grammatical variations thereof includes but it is not limited to a plurality of host cells, preferably mammalian host cells, suitably engineered and/or manipulated to express (i.e. to produce) one or more recombinant proteins maintained or grown in cell culture medium for a particular period of time, e.g. the production phase.

Mammalian cells, and in particular CHO cells, may be cultured in any medium that will support their growth and expression of the recombinant protein, preferably the medium is a medium that is free of animal-derived products such as animal serum and peptone. There are different cell culture media available to the person skilled in the art, each medium comprising different combinations of vitamins, amino acids, hormones, growth factors, ions, buffers, nucleosides, glucose or an equivalent energy source, present at appropriate concentrations to enable cell growth and protein production. Suitable media have e.g. been described in WO98/08934 and US2006/0148074 (both incorporated herein in their entirety). Further suitable commercially available media that could be used in the present invention or be modified to fulfil the cysteine/cysteine and/or tryptophan requirements include AmpliCHO CD medium, Dynamis™M Medium, EX-CELL® Advanced™M CHO Fed-batch System, CD FortiCHO™M medium, CP OptiCHO™ medium, Minimum Essential Media (MEM), BalanCD® CHO Growth A Medium, ActiPro™M medium, DMEM-Dulbecco's Modified Eagle Medium and RPMI-1640 medium.

Cell culture can take place in any suitable container such as a shake flask or a bioreactor, which may or may not be operated in a fed-batch mode depending on the scale of production required. These bioreactors may be either stirred-tank or air-lift reactors. Various large scale bioreactors are available with a capacity of more than 1,000 L to 50,000 L, preferably between 5,000 L and 20,000 L, or to 10,000 L. Alternatively, bioreactors of a smaller scale such as between 2 L and 100 L may also be used to manufacture an antibody or antibody fragment.

In a preferred embodiment of the present invention, irrespective of where any previous phase (i.e. an expansion phase) is carried out, the production phase is carried out in a bioreactor or any other suspension culture container such as shake flask or spinner flask. The production phase is operated preferably in a fed-batch mode, but any other mode such as batch, perfusion or chemostat modes can be used as an alternative. In the cases of a perfusion or chemostat the ratios of the total amounts of cysteine or cysteine and/or tryptophan used are calculated according to the perfusion flow rate versus the rate of removal of recombinant protein produced from the production vessel.

In one embodiment, the process comprises the step of recovering the recombinant protein from the cell culture medium and a further step of purifying the recombinant protein.

In a further embodiment, the purification comprises Protein A chromatography.

In a further embodiment, the process comprises a further the step of formulating the purified recombinant protein.

In one embodiment, the recombinant protein is formulated in a liquid formulation comprising one or more amino acids and a surfactant.

In a further embodiment, the formulation comprises histidine and/or proline.

In an even further embodiment, the formulation comprises histidine in a concentration of 5 mM to 100 mM, e.g. a concentration of 10 mM to 50 mM, and/or proline in a concentration of 100 mM to 500 mM, at a pH between 5 and 7.4, such as between 5 and 6.5, e.g. between 5 and 6, such as between 5.5 and 6.

In an even further embodiment, the formulation comprises histidine in a concentration of 30 mM and proline in a concentration of 250 mM, at a pH between 5.2 and 6.0, such as about 5.6.

In further embodiment, the surfactant is polysorbate 80, preferably in a concentration of 0.001% to 0.1% (w/v), e.g. 0.005% to 0.1%, such as 0.01% to 0.1%, e.g. 0.01% to 0.05%, such as 0.03%.

In an even further embodiment, the recombinant protein is an antibody and the antibody is formulated at a concentration of 10 mg/ml to 250 mg/ml, e.g. 20 mg/ml to 250 mg/ml, such as 50 mg/ml to 250 mg/ml, e.g. 120 mg/ml to 160 mg/ml, such as about 140 mg/ml.

The recombinant protein, e.g. an antibody or antigen-binding fragment, thereof is typically found in the supernatant of a mammalian cell culture, typically a CHO cell culture. For CHO host cells, the antibody or antigen-binding fragment thereof is secreted in the supernatant and said supernatant may be collected by methods known in the art, typically by centrifugation.

Recombinant proteins that can be produced using the process of the invention

The process of the invention can be used to produce any type of recombinant polypeptide or protein, including for example, peptides or larger proteins having significant tertiary structure as well as e.g. glycoproteins and multimeric proteins. However, preferably, the recombinant protein produced in the process according to the invention is an antibody or an antigen-binding fragment thereof. The term "antibody" or "antibodies" as used herein includes e.g. both monoclonal and polyclonal antibodies as well as both mono-specific and multispecific, such as bispecific, antibodies.

"Antibody" or "antibodies" include antibodies' of any species, in particular of mammalian species, typically having two heavy chains and two light chains, human antibodies of any isotype, including $IgA_1$, $IgA_2$, IgD, $IgG_1$, $IgG_{2a}$, $IgG_{2b}$, $IgG_3$, $IgG_4$ IgE, and IgM and modified variants thereof, non-human primate antibodies, e.g. from chimpanzee, baboon, rhesus or cynomolgus monkey, rodent antibodies, e.g. from mouse, rat or rabbit; goat or horse antibodies, and derivatives thereof, or of bird species such as chicken antibodies or of fish species such as shark antibodies. The term "antibody" or "antibodies" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences. "Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region or complementarity determining region (CDR) of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody performance. Humanization reduces the immunogenicity of non-human antibodies in humans, thus facilitating the application of antibodies to the treatment of human diseases. Humanized antibodies and several different technologies to generate them are well known in the art. The term "antibody" or "antibodies" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art. Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development are essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. The term "antibody" or "antibodies" as used herein, also refers to an aglycosylated antibody.

The term "antigen-binding fragment thereof" or grammatical variations thereof as used herein refers to an antibody fragment. A fragment of an antibody comprises at least one heavy or light chain immunoglobulin domain as known in the art and binds to one or more antigen(s). Examples of antibody fragments according to the invention include Fab, Fab', F(ab')$_2$, and Fv and scFv fragments; as well as diabodies, triabodies, tetrabodies, minibodies, domain antibodies (dAbs), such as sdAbs, VHH or camelid antibodies (e.g. from camels or llamas such as Nanobodies™) and VNAR fragments, single-chain antibodies, bispecific, trispecific, tetraspecific or multispecific antibodies formed from antibody fragments or antibodies, including but not limited to Fab-Fv or Fab-Fv-Fv constructs. Antibody fragments as defined above are known in the art.

In a particularly preferred embodiment, the antibody or antigen-binding fragment thereof produced through the methods according to the invention is (Table 1):
1) an antibody or antigen-binding fragment thereof which
   a. comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or
   b. comprises a light variable region having the sequence as defined in SEQ ID NO: 7 and a heavy variable region having the sequence as defined in SEQ ID NO: 8; or
   c. comprises a light variable region having at least 80% identity or similarity, preferably 90% identity or similarity to the sequence as defined in SEQ ID NO: 7 and a heavy variable region having at least 80% identity or similarity, preferably 90% identity or similarity to the sequence as defined in SEQ ID NO: 8;
   d. comprises a light variable region having the sequence as defined in SEQ ID NO: 7 and a heavy chain having the sequence as defined in SEQ ID NO: 11; or
   e. comprises a light variable region having at least 80% identity or similarity, preferably 90% identity or similarity to the sequence as defined in SEQ ID NO: 7 and a heavy chain having at least 80% identity or similarity, preferably 90% identity or similarity to the sequence as defined in SEQ ID NO: 11; or
2) an antibody which comprises a light chain having the sequence as defined in SEQ ID NO: 9 and a heavy chain having the sequence as defined in SEQ ID NO: 10; or
3) an antibody which comprises a light chain having at least 80% identity or similarity, preferably 90% identity or similarity to the sequence as defined in SEQ ID NO: 9 and a heavy chain having at least 80% identity or similarity, preferably 90% identity or similarity to the sequence as defined in SEQ ID NO: 10.

Throughout this specification, complementarity determining regions ("CDR") are defined according to the Kabat definition. The Kabat definition is a standard for numbering the residues in an antibody and it is typically used to identify CDR regions (Kabat et al., (1991), 5th edition, NIH publication No. 91-3242).

TABLE 1

| Region and SEQ ID identifier | Amino acid sequence |
| --- | --- |
| CDR-H1 SEQ ID NO: 1 | GFTFSNYGMV |
| CDR-H2 SEQ ID NO: 2 | YIDSDGDNTYYRDSVKG |

TABLE 1-continued

| Region and SEQ ID identifier | Amino acid sequence |
|---|---|
| CDR-H3 SEQ ID NO: 3 | GIVRPFLY |
| CDR-L1 SEQ ID NO: 4 | KSSQSLVGASGKTYLY |
| CDR-L2 SEQ ID NO: 5 | LVSTLDS |
| CDR-L3 SEQ ID NO: 6 | LQGTHFPHT |
| Light variable region SEQ ID NO: 7 | DIQMTQSPSS LSASVGDRVT ITCKSSQSLV GASGKTYLYW LFQKPGKAPK RLIYLVSTLD SGIPSRFSGS GSGTEFTLTI SSLQPEDFAT YYCLQGTHFP HTFGQGTKLE IK |
| Heavy variable region SEQ ID NO: 8 | EVPLVESGGG LVQPGGSLRL SCAVSGFTFS NYGMVWVRQA PGKGLEWVAY IDSDGDNTYY RDSVKGRFTI SRDNAKSSLY LQMNSLRAED TAVYYCTTGI VRPFLYWGQG TLVTVS |
| Light chain SEQ ID NO: 9 | DIQMTQSPSS LSASVGDRVT ITCKSSQSLV GASGKTYLYW LFQKPGKAPK RLIYLVSTLD SGIPSRFSGS GSGTEFTLTI SSLQPEDFAT YYCLQGTHFP HTFGQGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| Heavy chain SEQ ID NO: 10 | EVPLVESGGG LVQPGGSLRL SCAVSGFTFS NYGMVWVRQA PGKGLEWVAY IDSDGDNTYY RDSVKGRFTI SRDNAKSSLY LQMNSLRAED TAVYYCTTGI VRPFLYWGQG TLVTVSSAST KGPSVFPLAP CSRSTSESTA ALGCLVKDYF PEPVTVSWNS GALTSGVHTF PAVLQSSGLY SLSSVVTVPS SSLGTKTYTC NVDHKPSNTK VDKRVESKYG PPCPPCPAPE FLGGPSVFLF PPKPKDTLMI SRTPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLGK |
| Fab heavy chain SEQ ID NO: 11 | EVPLVESGGG LVQPGGSLRL SCAVSGFTFS NYGMVWVRQA PGKGLEWVAY IDSDGDNTYY RDSVKGRFTI SRDNAKSSLY LQMNSLRAED TAVYYCTTGI VRPFLYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC |

The recombinant protein or the preferred antibody or antigen-binding fragment thereof may be typically produced by host cells containing a vector encoding the protein or antibody nucleotide sequence.

Antibodies or antigen-binding fragment thereof may comprise only a heavy or light chain protein, in which case only a heavy chain or light chain protein coding sequence needs to be used to transfect the cells. For production of products comprising both heavy and light chains, the cells may be transfected with two vectors, a first vector encoding a light chain protein and a second vector encoding a heavy chain protein. Alternatively, a single vector may be used, the vector including sequences encoding light chain and heavy chain proteins.

In a preferred embodiment, the invention provides for a process for producing an antibody or antigen-binding fragment thereof protein comprising:
- culturing CHO cells capable of producing an antibody or antigen-binding fragment thereof in a medium;
- progressing the culture through a production phase wherein the antibody or antigen-binding fragment thereof is produced by the cells, wherein, during said production phase, the culture is supplemented with cysteine or cystine up to a total amount of from 10 wt % to 30 wt % of the expected total amount of antibody or antibody-binding fragment thereof produced,
- and, optionally, recovering the antibody or antigen-binding fragment thereof from the cell culture medium,
- wherein the total amount of cysteine or cystine provided during the process is from 2.9 to 12 g/($10^{12}$ cells), such as from 2.9 to 7 g/($10^{12}$ cells), e.g. from 5.6 to 7 g/($10^{12}$ cells), wherein cells refers to the expected integral viable cell count at the end of the production phase, and
- wherein cysteine or cystine is provided through daily addition during the production phase, and
- wherein the cysteine or cystine concentration in the cell culture medium does not exceed 0.9 g/L at any time point during the production phase, preferably wherein the cysteine or cystine concentration in the cell culture medium does not exceed 0.3 g/L at any time point during the production phase, and
- wherein said antibody or antigen-binding fragment thereof preferably:
- comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or comprises a light variable region having the sequence as defined in SEQ ID NO: 7 and a heavy variable region having the sequence as defined in SEQ ID NO: 8. heavy variable region having the sequence as defined in SEQ ID NO: 8.

In a further preferred embodiment, the invention provides for a process for producing an antibody or antigen-binding fragment thereof comprising:
a. culturing CHO cells capable of producing an antibody or antigen-binding fragment thereof in a medium;
b. progressing the culture through a production phase wherein the antibody or antigen-binding fragment thereof is produced by the cells, wherein, during said production phase, the cell culture medium is supplemented with
cysteine or cystine up to a total amount of from 10 wt % to 30 wt % of expected total amount of antibody or antigen-binding fragment thereof produced; and/or
tryptophan up to a total amount of from 8 wt % to 35 wt % of expected total amount of antibody or antigen-binding fragment thereof produced,
c. and, optionally, recovering the antibody or antigen-binding fragment thereof from the cell culture medium,
wherein the total amount of cysteine or cystine provided during the process is from 2.9 to 12 g/($10^{12}$ cells), such as from 2.9 to 7 g/($10^{12}$ cells), e.g. from 5.6 to 7 g/($10^{12}$ cells), wherein cells refers to the expected integral viable cell count at the end of the production phase, and
wherein the total amount of tryptophan provided during the process is from 2.5 to 7 g/($10^{12}$ cells), such as from 2.5 to 3.5 g/($10^{12}$ cells/L), wherein cells refers to the expected integral viable cell count at the end of the production phase, and
wherein cysteine or cystine and/or tryptophan are provided through daily addition during the production phase, and
wherein the cysteine or cystine concentration in the cell culture medium does not exceed 0.9 g/L at any time point during the production phase, preferably wherein the cysteine or cystine concentration in the cell culture medium does not exceed 0.3 g/L at any time point during the production phase, and
wherein the tryptophan concentration in the cell culture does not exceed 0.6 g/L medium at any time point during the production phase, preferably wherein the tryptophan concentration in the cell culture medium does not exceed 0.3 g/L at any time point during the production phase, and
wherein said antibody or antigen-binding fragment thereof preferably:
1) comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or
2) comprises a light variable region having the sequence as defined in SEQ ID NO: 7 and a heavy variable region having the sequence as defined in SEQ ID NO: 8.

The invention will now be further described by way of examples with references to embodiments illustrated in the accompanying drawings.

EXAMPLES

Abbreviations mAb: monoclonal antibody; MFCS: multi-fermentation control system; Cys: cysteine or cystine; Trp: tryptophan Materials and Methods Cell Line, Cell Culture and Experimental Procedure A CHO-DG44 cell line was used. The cells were cultivated in chemically-defined animal-free inoculation media containing cystine (0.05 g/L) and tryptophan (0.2 g/L) under standard operating conditions (pH 7, temperature 36.8° C.) in 2 L stirred tank glass bioreactor with supply towers (C-DCUII, Sartorius Stedim Biotech) controlled by a multi-fermentation control system (Sartorius Stedim Biotech). Four different production cell lines were used, each producing a monoclonal antibody (mAb) termed mAb1, mAb2, mAb3 and mAb4, respectively. mAb1 is an anti-FcRn antibody comprising a light chain having the sequence as defined in SEQ ID NO: 9 and a heavy chain having the sequence as defined in SEQ ID NO: 10.

The production was operated in fed batch-experiment mode for 14 days. During this phase, the monoclonal antibodies are secreted into the medium. Samples were drawn daily to determine viable cell density (VCD), viability, off-line pH, pCO2, osmolality, glucose-lactate concentration, amino acid concentration and mAb concentration (stocked at −80° C.). Antifoam was added manually on demand every day to control the build-up of foam. 72 hours after inoculation, continuous nutrient feeding was started with a predetermined rate. The continuous nutrient feeding medium does not comprise cysteine/cystine or tryptophan. At this time, cysteine/cystine and tryptophan was added daily during 10 days as a bolus feed having the amount as described in the examples below. The amount of cysteine/cystine and tryptophan described in the examples is the total amount of the bolus additions starting 72 hours after inoculation taking into account the initial amount of these amino acids already present in the inoculation medium. A glucose bolus feed was added to the culture when the glucose concentration dropped below 6 g/L (from day 6 onwards) and glucose concentrations were measured daily. Samples for the amino acid analysis were taken before the feed addition. The concentrations after feeding were computed based on the feed composition and measured nutrients concentration before feed addition.

Analytical Methods

Cell were counted by using a VI-CELL® XR (Beckman-Coulter, Inc., Brea, Calif.) automated cell counting device operate that operated based on trypan blue exclusion.

Glucose and lactate levels in the culture medium were determined using a NOVA 400 BioProfile automated analyser (Nova Biomedical, Waltham, Mass.).

A model 2020 freezing-point osmometer (Advanced Instruments, Inc., Norwood, Mass.) was used for osmolality determination. Offline gas and pH measurements were performed with a model BioProfile pHOx® blood gas analyser (Nova Biomedical Corporation, Waltham, Mass.).

Metabolites concentrations were determined daily using a CedexBioHT system (Roche).

Product titer analysis was performed with a ForteBio Octet model analyser (ForteBio, Inc., Menlo Park, Calif.) or protein A high-pressure liquid chromatography (HPLC) with cell culture supernatant samples which were stored at −80° C. prior to analysis.

Amino acids were analysed by reversed-phase UPLC (Waters AccQ.Tagultra method) after ultra-filtration using Amicon Ultra-0.5 mL centrifugal filters (Merck Millipore, Billerica, Mass.).

Protein A purification (AKTA Xpress system) was employed to purify mAb in the cell culture supernatant samples. The relative percentage of main, acidic (APG for Acidic Peak Group) and basic (BPG for Basic Peak Group) isoform of the purified mAb was determined by Imaged Capillary Electrophoresis (ProteinSimple iCE3). High Molecular Weight Species (HMWS), monomer and Low Molecular Weight Species (LMWS) levels of the purified mAb were determined by size exclusion chromatography (SE-UPLC).

Colour intensity of formulations of concentrated mAb1 and mAb2 was measured in the concentrated protein A eluates using a spectrophotometer by transmission (UltrascanPro) and compared to the Commission Internationale de L'éclairage (CIL) scale. The numerical results were normalized to the concentration of 40 mg/mL.

Electrospray ionization mass spectrometry (ESI-MS) was performed on purified mAb1. Peptide mapping was carried out in order to identify post translational modifications on the antibodies. Statistical analysis was performed using SAS software JMP 11.

Example 1

Two litres bioreactors were inoculated with CHO cells producing mAb1 at a seeding density of $0.35 \times 10^6$ cells/mL. Eight experimental conditions were tested in fed-batch process as described in the Materials and Methods section, with various maximum concentrations of cysteine or cystine and tryptophan reached throughout cell culturing and various total amounts of cysteine or cystine (Cys) and tryptophan (Trp) wt % of total mAb1 weight produced (Table 2a). The first objective was to assess the impact of cysteine or cystine and tryptophan on the heterogeneity of the recombinant mAb1. The second objective was to identify if the impact was due to high concentrations of cysteine or cystine and/or tryptophan reached throughout cell culturing and/or due to the total quantity added wt % of total mAb weight produced.

TABLE 2a

| Bioreactor ID | Cys max concentration | Total amount Cys/mAb1 wt % (g/g) | Trp max concentration | Total amount Trp/mAb1 wt % (g/g) |
|---|---|---|---|---|
| 1 | 0.05 g/L | 17.51 | 0.20 g/L | 11.79 |
| 2 | 0.05 g/L | 13.35 | 0.20 g/L | 10.34 |
| 3 | 0.30 g/L | 15.72 | 0.30 g/L | 10.58 |
| 4 | 0.05 g/L | 18.94 | 0.20 g/L | 11.27 |
| 5 | 0.12 g/L | 16.18 | 0.20 g/L | 9.87 |
| 6 | 0.05 g/L | 13.30 | 0.20 g/L | 8.96 |
| 7 | 0.05 g/L | 20.79 | 0.20 g/L | 12.37 |
| 8 | 0.05 g/L | 20.840612 | 0.20 g/L | 8.5684363 |

The recombinant protein charge variants and colour intensity were measured as described in materials and methods section. Data were analysed by one way Anova statistical analysis for a linear fit and p-values <0.05 were considered acceptable.

As shown in FIG. 2B there was a correlation between an increased acidic peak group charge variant in mAb1 (APG %) and an increase of the total amount of cysteine or cystine added per total mAb1 weight % (g/g) produced.

With respect to the mAb1 colour intensity, there was a correlation between an increased mAb1 colour intensity (b* value normalized to 40 mg/mL) and an increased total amount of tryptophan added per total mAb1 weight % (g/g) produced (FIG. 2A).

However, when the data were analysed with respect to the maximum concentration of tryptophan or cysteine or cystine, there was no impact on the colour or APG (FIGS. 2C and 2D).

Figure 3B:
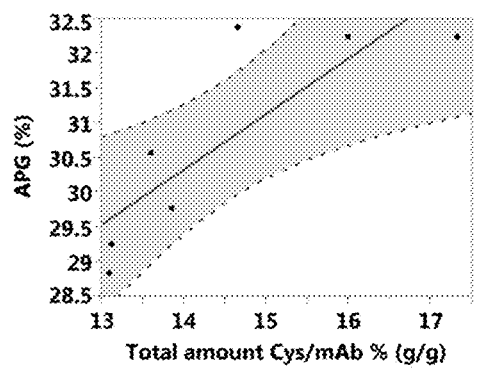
Figure 3C:
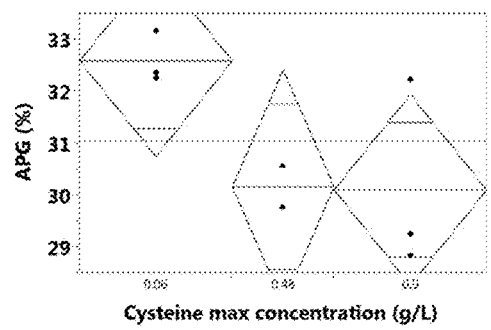
Figure 3D:
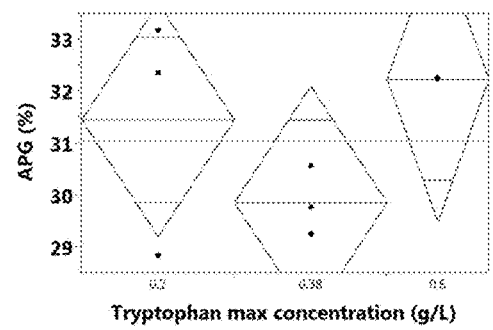

In order to confirm that it is the total quantity of cysteine or cystine and tryptophan per total mAb1 weight produced that affects the heterogeneity of mAb1 and not the maximum concentration of cysteine or cystine and/or tryptophan reached throughout the production phase in a fed-batch setting, 8 experimental conditions were tested with various bolus additions of cysteine or cystine and tryptophan on day 3 in order to reach high concentrations of the 2 amino acids (Table 2b). In order to have the same quantity of cysteine or cystine and tryptophan added wt % (g/g) of total mAb1 weight produced, the feeding strategy was adapted. As shown in the fed-batch conditions, there is a correlation between an increased acidic peak group charge variant in mAb 1 (APG %) and an increase of the total amount of cysteine or cystine added per total mAb1 wt % (g/g) produced (FIG. 3B) and between an increased mAb1 colour intensity (b* value normalized to 40 mg/mL) and an increased total amount of tryptophan added per total mAb1 weight % (g/g) produced (FIG. 3A). However, there was no correlation with APG charge variant and maximum concentrations (g/L) of cysteine or cystine and tryptophan (FIGS. 3C and 3D, respectively). These results confirm that the total amount of cysteine and tryptophan added during cell culturing per wt % (g/g) of total mAb1 weight produced impact the APG charge variant and the colour intensity. The maximum concentration of cysteine or cystine and tryptophan do not impact the APG charge variant and the colour intensity.

TABLE 2b

| Bioreactor ID | Cys maximum concentration (g/L) | Trp maximum concentration (g/L) | Total amount Cys/mAb1 wt % (g/g) | Total amount Trp/mAb1 wt % (g/g) |
|---|---|---|---|---|
| 9 | 0.06 | 0.20 | 13.85 | 9.34 |
| 10 | 0.06 | 0.60 | 17.31 | 11.71 |
| 11 | 0.90 | 0.60 | 16.00 | 10.79 |
| 12 | 0.48 | 0.38 | 13.60 | 9.17 |
| 13 | 0.90 | 0.38 | 13.12 | 8.88 |
| 14 | 0.90 | 0.20 | 13.10 | 8.84 |
| 15 | 0.06 | 0.20 | 14.66 | 9.88 |
| 16 | 0.48 | 0.38 | 13.85 | 9.37 |

CONCLUSIONS

The total quantity added of Cys and Trp wt % of total recombinant mAb1 (g/g) produced has an impact the mAb1 charge variant and colour intensity. On the contrary, the maximum concentration of cysteine or cystine and tryptophan in the cell culture medium did not impact mAb1 quality.

Example 2

In order to further investigate the impact of the total quantity of cysteine or cystine and tryptophan added wt % of total mAb produced (g/g), during a cell culturing, 48 experimental conditions (Table 3) in 2 L bioreactors runs, were prepared as described in the methods' section. The mAb1 charge variant, aggregates (HMWS), colour intensity, titer and viable cell growth were analyzed.

TABLE 3

| Bioreactor ID | Total amount Cys/mAb1 % (g/g) | Total amount Trp/mAb1 % (g/g) |
|---|---|---|
| 17 | 10.39 | 26.31 |
| 18 | 10.46 | 26.50 |
| 19 | 10.00 | 5.06 |
| 20 | 14.08 | 71.33 |
| 21 | 47.60 | 4.82 |
| 22 | 45.43 | 4.60 |
| 23 | 25.31 | 12.82 |
| 24 | 25.51 | 12.92 |
| 25 | 25.03 | 12.68 |
| 26 | 41.45 | 42.00 |
| 27 | 40.71 | 41.24 |
| 28 | 27.20 | 13.78 |
| 29 | 24.31 | 12.31 |
| 30 | 70.80 | 17.93 |
| 31 | 69.81 | 17.68 |
| 32 | 85.88 | 4.35 |
| 33 | 236.11 | 119.60 |
| 34 | 11.75 | 14.88 |
| 35 | 14.02 | 14.21 |
| 36 | 10.24 | 15.56 |
| 37 | 10.31 | 26.10 |
| 38 | 18.35 | 15.49 |
| 39 | 32.60 | 5.50 |
| 40 | 10.21 | 5.17 |
| 41 | 22.62 | 6.87 |
| 42 | 51.03 | 5.17 |
| 43 | 14.81 | 7.50 |
| 44 | 21.61 | 10.95 |
| 45 | 13.79 | 6.99 |
| 46 | 32.08 | 14.63 |
| 47 | 23.85 | 12.40 |
| 48 | 23.02 | 10.50 |
| 49 | 21.37 | 9.75 |
| 50 | 23.90 | 10.65 |
| 51 | 23.82 | 12.10 |
| 52 | 31.33 | 15.85 |
| 53 | 25.53 | 16.10 |
| 54 | 24.22 | 10.41 |
| 55 | 14.66 | 7.42 |
| 56 | 21.63 | 10.60 |
| 57 | 13.05 | 6.60 |
| 58 | 16.31 | 8.28 |
| 59 | 15.08 | 7.62 |
| 60 | 12.82 | 6.48 |
| 61 | 12.36 | 6.27 |
| 62 | 12.35 | 6.24 |
| 63 | 13.81 | 6.98 |
| 64 | 13.05 | 6.62 |

Figure 4:
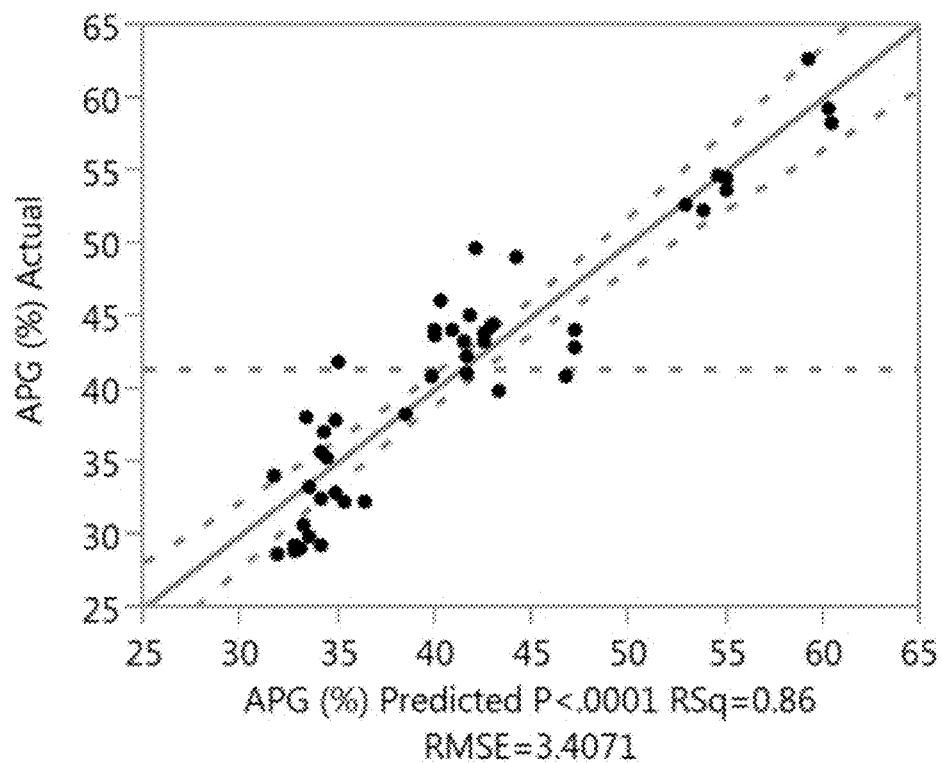
FIG. 4: Multiple linear regression model of the acidic peak group (APG) variant of the recombinant monoclonal antibody mAb1 as a function of cysteine or cystine and tryptophan total quantity added wt % of total mAb1 produced (g/g).

As shown in FIG. 4, the total quantity of cysteine or cystine and tryptophan added throughout a production phase wt % of total mAb1 (g/g) produced impacts the acidic charge variant group (APG %). There is a saturation effect around 50 wt % of total quantity of cysteine or cystine added throughout production phase of 14 days per total mAb1 (g/g) produced. The impact of cysteine or cystine and tryptophan is cumulative with no interaction. Decreasing the percentage of total quantity of cysteine or cystine and tryptophan added throughout a production phase of 14 days wt % of total mAb1 (g/g) produced decreases the percentage of acidic peak on mAb1 produced.

Figure 5:
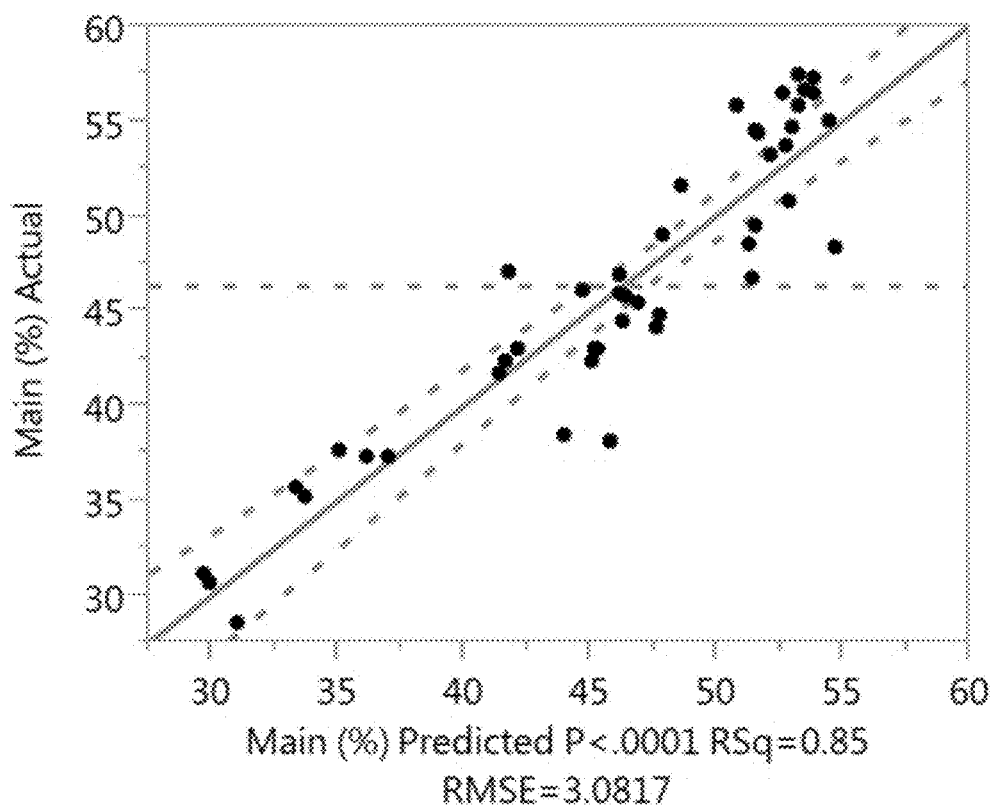
FIG. 5: Multiple linear regression model of the main peak group variant of the recombinant monoclonal antibody mAb1 as a function of cysteine or cystine and tryptophan total quantity added wt % of total recombinant mAb1 produced (g/g).

FIG. 5 shows the impact of the total quantity of cysteine or cystine and tryptophan (added throughout 14 days cell culturing) wt % of total mAb1 weight produced on main peak group. As seen for the APG %, the impact of cysteine or cystine and tryptophan is cumulative with no interaction. Decreasing the total quantity of cysteine or cystine and tryptophan added throughout a production phase of 14 days wt % of total mAb1 weight produced increases the percentage of main peak on the recombinant mAb produced.

Figures 6, 7:
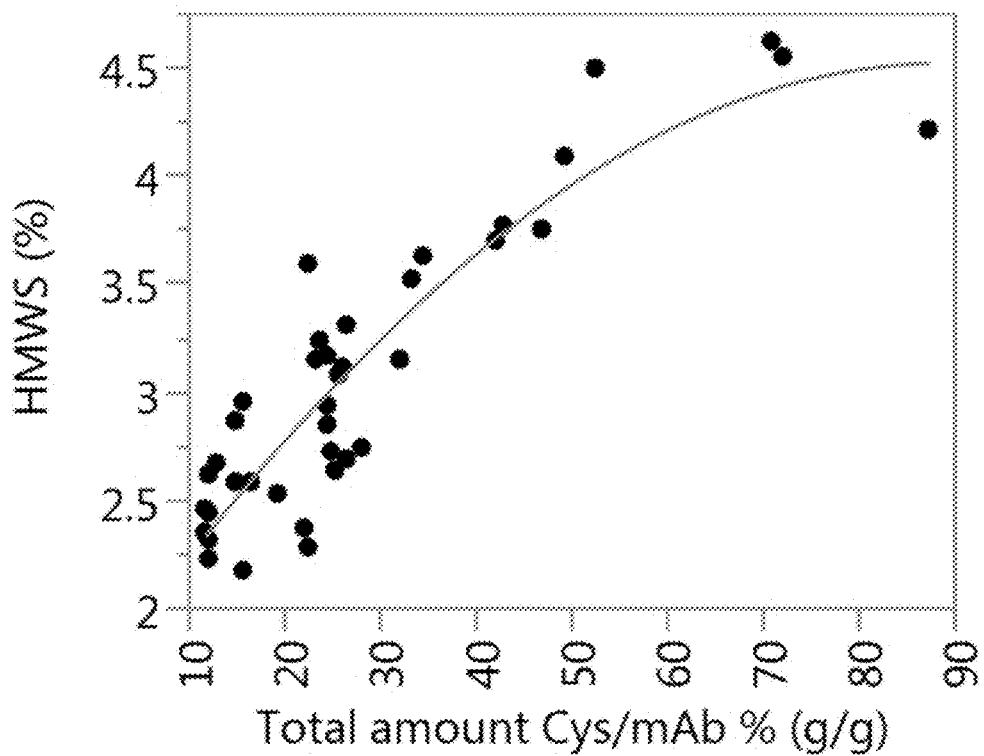
FIG. 6: Multiple linear regression model of the high molecular weight species (HMWS) variant of the recombinant monoclonal antibody mAb1 as a function of cysteine or cystine total quantity added wt % of total recombinant mAb1 produced (g/g).
FIG. 7: Multiple linear regression model of the b* value normalized to 40 mg/mL variant of the recombinant monoclonal antibody mAb1 as a function of cysteine or cystine and tryptophan total quantity added wt % of total recombinant mAb1 produced (g/g).
Figure 8A:
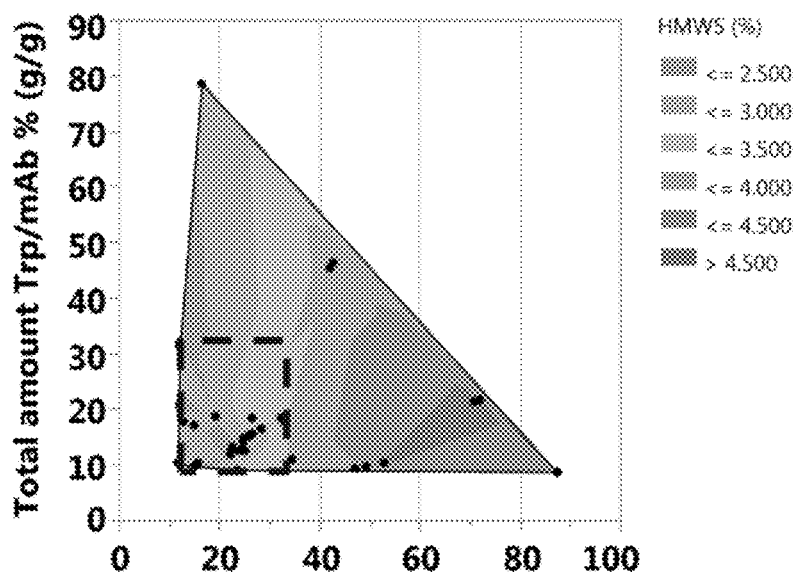
FIGS. 8A-8D: Contour plots of the impact of cysteine or cystine and tryptophan total quantity added wt % of total recombinant mAb1 produced (g/g) on (FIG. 8A) high molecular weight species (HMWS) and (FIG. 8B) b* value normalized to 40 mg/mL (FIG. 8C) acidic peak group (APG) and (FIG. 8D) main peak group variants. The dashed black line square corresponds to the ideal cysteine or cystine and tryptophan total quantity added wt % of total recombinant mAb1 produced (g/g) in order to reduce APG, HMWS, b* value normalized to 40 mg/mL and increase main peak group variant which correspond to a quantity added of 12.06 and 28.03 wt % of total mAb1 (g/g) produced for cysteine or cystine and between 8.84 and 32.06 wt % of total mAb1 (g/g) produced for tryptophan.
Figure 8B:
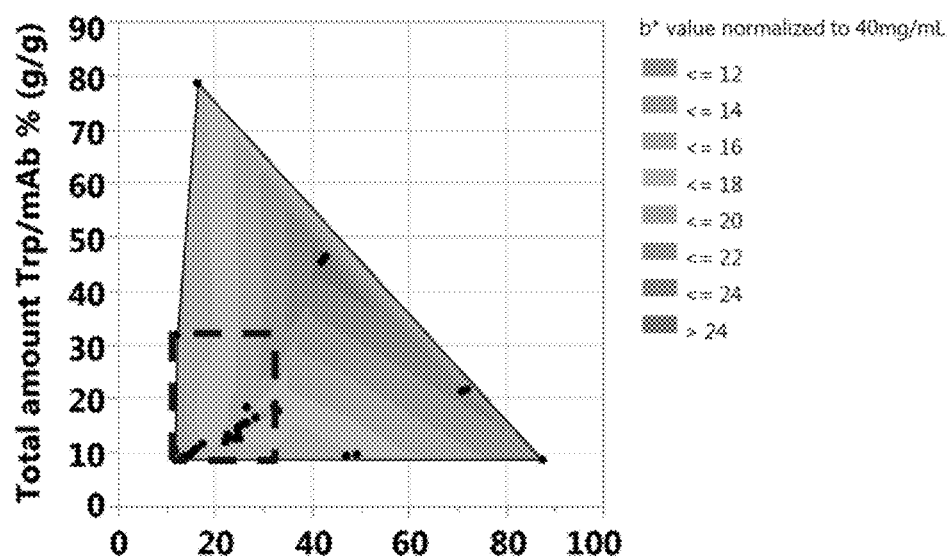
Figure 8C:
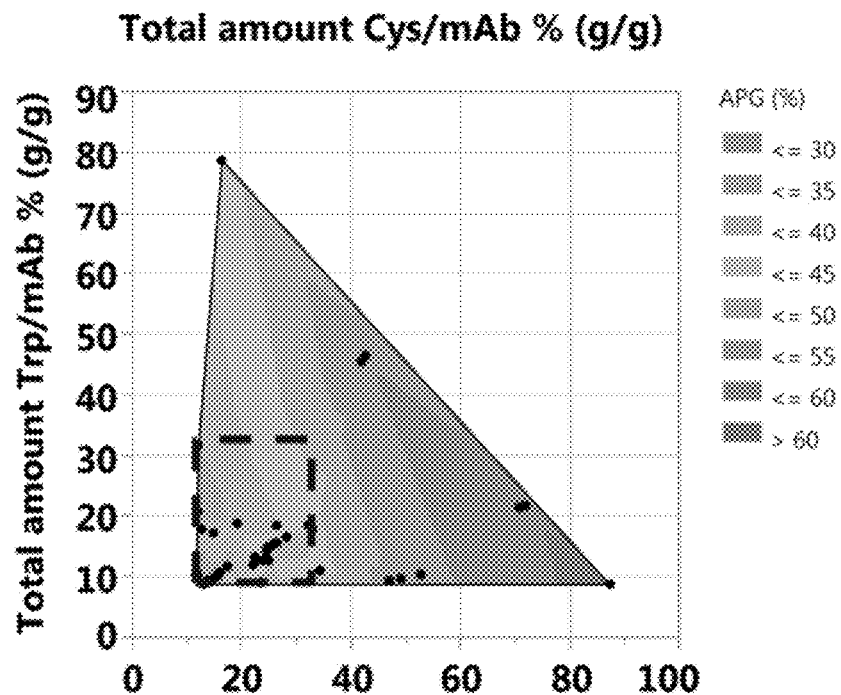
Figure 8D:
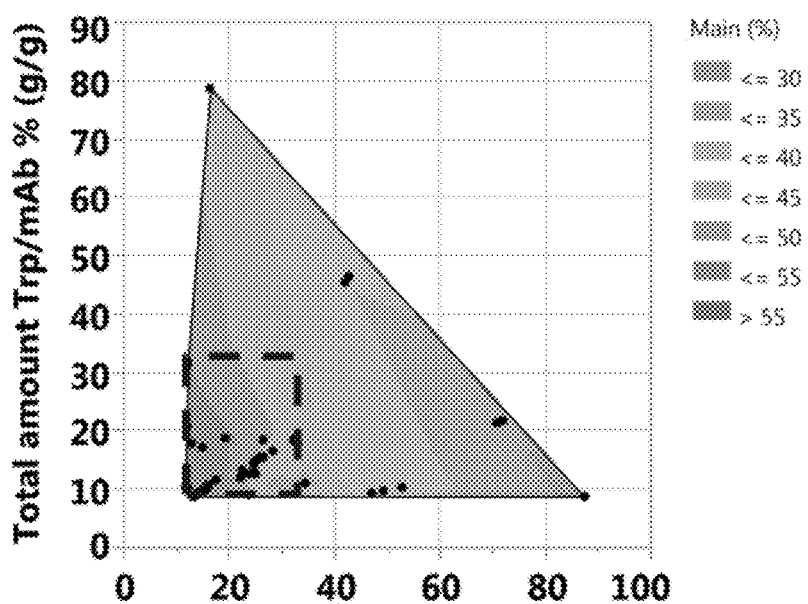

FIG. 6 shows the impact of the total quantity of cysteine or cystine added throughout a production phase of 14 days wt % of total mAb1 (g/g) produced on high molecular weight species (HMWS). There is a saturation effect around 50% of total quantity of cysteine or cystine added throughout a production phase of 14 days wt % of total mAb1 (g/g) produced. Decreasing the total quantity of cysteine or cystine reduces the percentage of HMWS on the recombinant mAb produced. No impact of total quantity of Trp added is observed on HMWS.

The results shown in FIG. 7 illustrate the impact of the total quantity of cysteine or cystine and tryptophan added throughout a production phase of 14 days wt % of total mAb1 (g/g) produced on colour intensity (b-value normalized to 40 mg/mL) of the recombinant mAb1. Decreasing the total quantity of cysteine or cystine and tryptophan added throughout the production phase of 14 days reduces the colour intensity of the recombinant mAb1 produced. There is an interaction effect between cysteine or cystine and tryptophan total quantity added throughout a production phase of 14 days wt % of total mAb1 (g/g) produced.

FIGS. 8A-8D show contour plots illustrating optimum ranges of the percentage of total quantity of cysteine or cystine and tryptophan added throughout a production phase of 14 days wt % of total mAb-1 (g/g) produced for achieving the lowest values of APG, HMWS, colour intensity and the highest values for main peak group; the total quantity of cysteine or cystine and tryptophan added between 12.06 and 28.03 wt % of total mAb-1 (g/g) produced for cysteine or cystine and between 8.84 and 32.06 wt % of total mAb1 (g/g) produced for tryptophan.

Figure 9A:
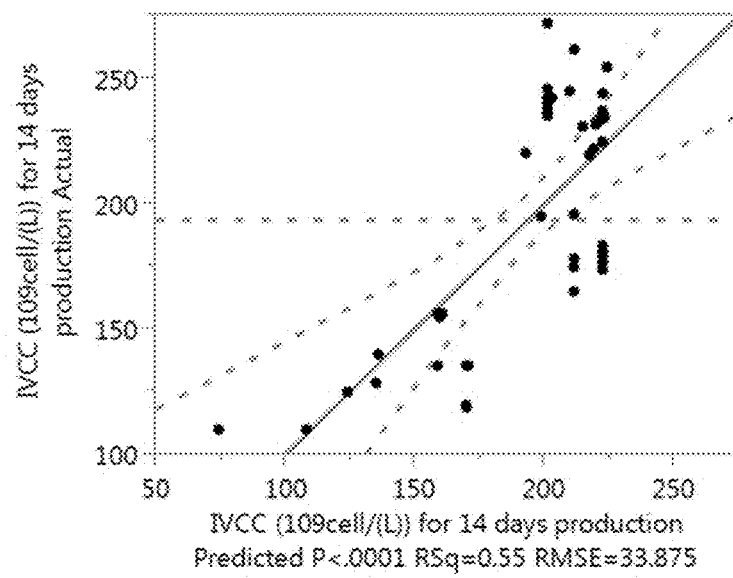
FIGS. 9A-9B: Impact of cysteine or cystine and tryptophan total quantity added wt % of the cell culture volume (CSV) weight on integral viable cell count (IVCC) normalized to the CSV. A multiple linear regression model of the cumulative IVCC normalized to the CSV as a function of cysteine or cystine and tryptophan total quantity added wt % of the CSV weight is shown in FIG. 9A. Contour plot of the impact of cysteine or cystine and tryptophan total quantity added wt % of the CSV weight on the cumulative IVCC normalized to the CSV is shown in FIG. 9B.
Figure 9B:
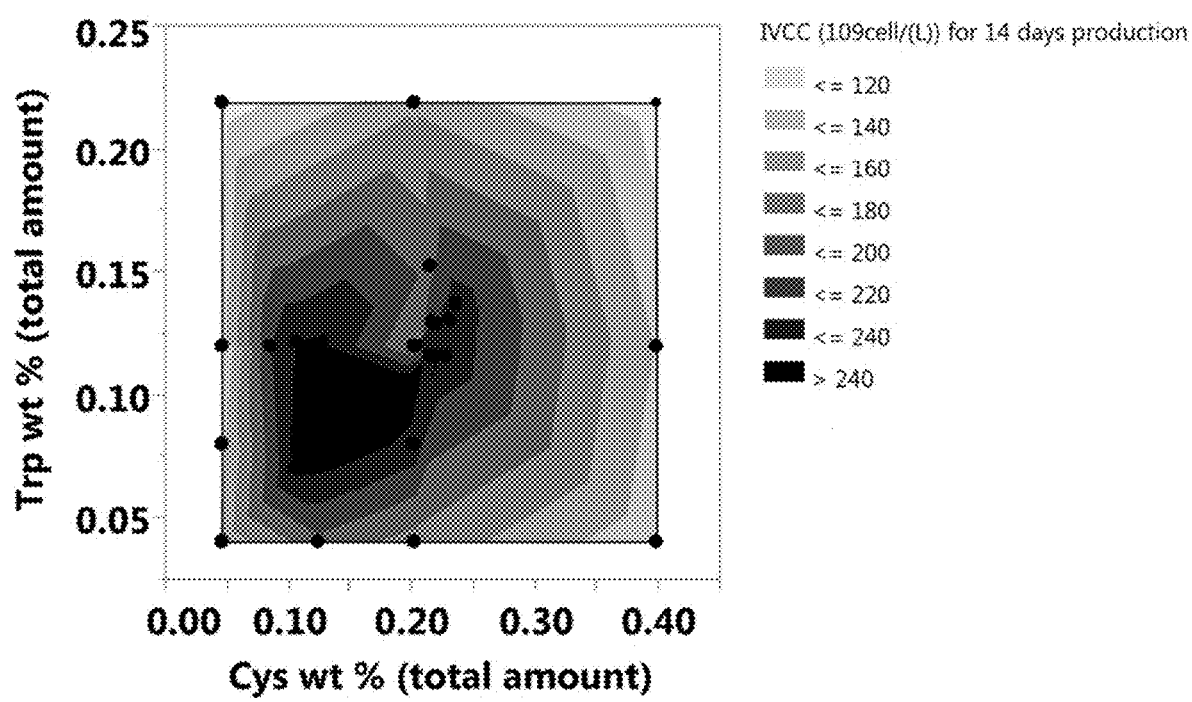

The cumulative integral viable cell count (IVCC) throughout a production phase of 14 days was computed and normalized by the cell culture volume (CSV). The results shown in FIGS. 9A and 9B show an impact of percentage of total amount of cysteine or cystine and tryptophan added to the cell culture medium per initial CSV weight on the IVCC. There are optimum ranges of percentage of total weight of cysteine or cystine and tryptophan added to the cell culture medium per initial CSV weight which are between 0.08% and 0.24% for cysteine or cystine and between 0.07% and 0.15% for tryptophan. No synergistic, only cumulative, effect was observed (FIGS. 9A and 9B).

Figure 10A:
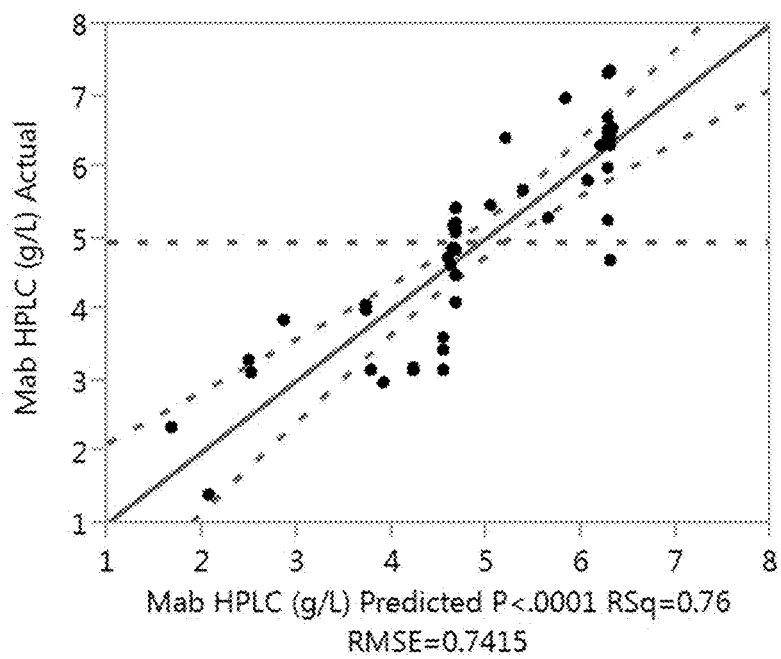
FIGS. 10A-10B: Impact of total amount of cysteine or cystine and tryptophan added to the cell culture medium during production phase wt % of the CSV weight on final mAb1 titer measured by HPLC method (mAb HPLC). A multiple linear regression model of the final mAb1 HPLC titer as a function of cysteine or cystine and tryptophan total quantity added wt % of the CSV weight is shown in FIG. 10A. Contour plot of the impact of cysteine or cystine and tryptophan total quantity added wt % of the CSV weight on final mAb HPLC titer is shown in FIG. 10B.
Figure 10B:
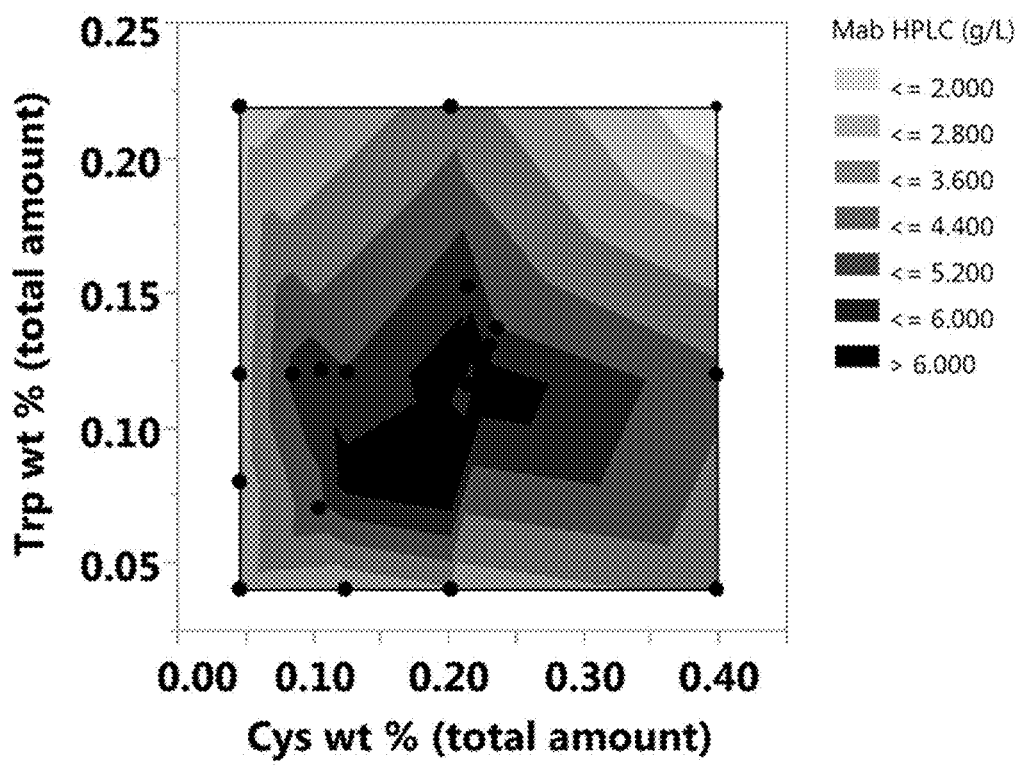

FIGS. 10A and 10B show the impact of percentage of total amount of cysteine or cystine and tryptophan added to the cell culture medium per initial CSV weight on the mAb1 titer. There is an optimum range of percentage of total amount of cysteine or cystine and tryptophan added to the cell culture medium per CSV weight which is between 0.08% and 0.24% for cysteine or cystine and between 0.07% and 0.15% for tryptophan wt % of CSV weight. There is no interaction effect.

The contour plots shown in FIGS. 11A and 11B show the optimum ranges of total amount of cysteine or cystine and tryptophan added to the cell culture medium per IVCC*10$^{-12}$ at the end of the production phase which are between 2.9 and 12 g for Cys and between 2.5 and 7 g for Trp.

Example 3

The recombinant monoclonal antibody was characterized for 3 fed-batch experimental conditions as described in material and methods with various cysteine or cystine and tryptophan total quantity added wt % of total recombinant mAb1 produced (Table 4).

TABLE 4

| Bioreactor ID | Total amount Cys/mAb1 wt % (g/g) | Total amount Trp/mAb1 wt % (g/g) |
|---|---|---|
| 65 | 11.72 | 7.21 |
| 66 | 22.16 | 11.89 |
| 67 | 94.20 | 46.72 |

Mass spectroscopy analysis indicated a mass shift of the most intense peak observed in the mass spectrum in non-denaturing and denaturing conditions and for the glycosylated mAb1 as a result of increasing the concentration of cysteine or cystine and tryptophan. Those observations lead to the conclusion that the modifications are not linked to alterations of glycosylation patterns. Analysis of the light chain, heavy chain and halfmer (one heavy chain plus one light chain) of mass spectrum after manual deconvolution suggests that a possible glycation of the mAb1 occurs with high total quantity of cysteine or cystine and tryptophan added throughout a production phase of 14 days wt % of total mAb weight produced. Possibly more adducts, i.e. additions of small molecules on mAb1, can be observed. Cysteine adduction on the light chain increases when the total quantity added of cysteine or cystine and tryptophan are also increasing. Table 5 shows the summary of the characteristics of the mAb1, obtained by Peptide Mapping, for the three experimental conditions tested. Results show that increasing the total quantity of cysteine or cystine and tryptophan added throughout a production phase of 14 days wt % of total mAb weight produced lead to an increase of methionine oxidation at threonine 19 of heavy chain and deamidation at threonine 33 of the heavy chain. Moreover, the APG % and the BPG % variants of mAb1 dramatically increase with the increase of cysteine or cystine and tryptophan total quantity added throughout a production phase of 14 days wt % of total mAb weight produced, whilst the main peak increases with the decreasing of cysteine or cystine and tryptophan total quantity added throughout a production phase of 14 days wt % of total mAb weight produced.

TABLE 5

| mAb1 characteristics | Bioreactor ID | | |
|---|---|---|---|
| | 65 | 66 | 67 |
| Meth. Ox HC T019 | 10.60% | 15.20% | 19.70% |
| Deamidation HC T023 | 2.60% | 2.10% | 2.20% |
| Deamidation HC T033 | 4.80% | 6.60% | 7.00% |
| APG (%) | 39.30% | 49.10% | 82.90% |
| BPG (%) | 6.10% | 7.30% | 2.40% |
| Main (%) | 54.70% | 43.70% | 14.80% |

Example 4

Figure 12:
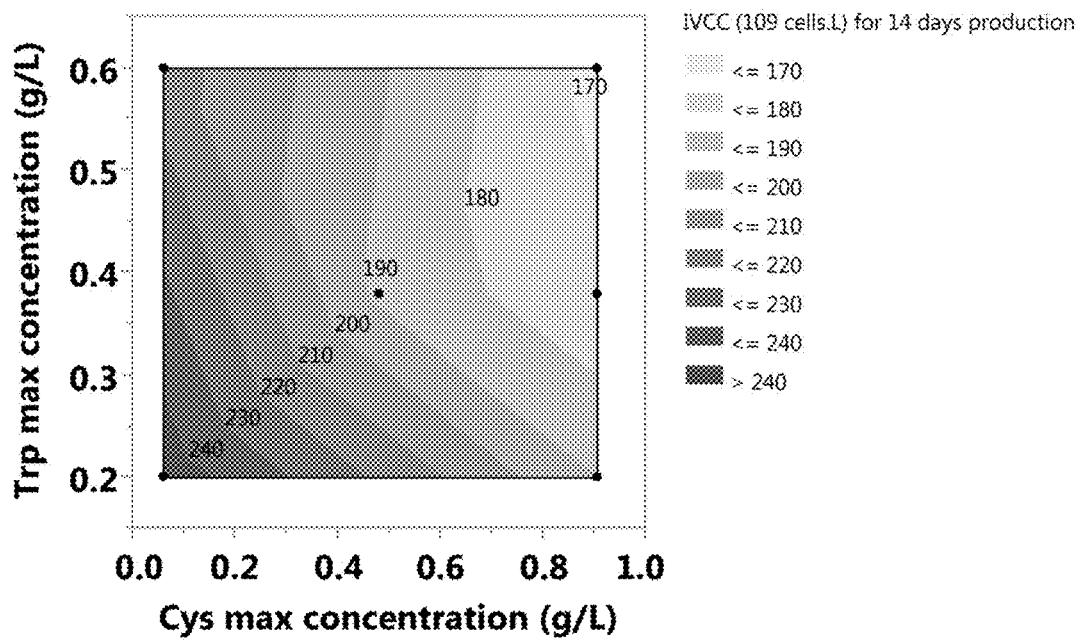

In order to identify inhibitory concentrations of cysteine or cystine and tryptophan on the growth of a DG44 CHO cell line expressing mAb1, various bolus additions of cysteine or cystine and tryptophan on day 3 were tested with the aim of reaching high concentrations of those amino acids (Table 2b). In order to have the same quantity of cysteine or cystine and tryptophan added wt % of total mAb1 weight produced, the feeding strategy was adapted. FIG. 12 shows that high concentrations of cysteine or cystine and tryptophan from 0.3 g/L up to 0.9 g/L and 0.6 g/L, respectively, reduce significantly the cell growth (cumulative IVCC throughout a production phase of 14 days normalized by the CSV).

Example 5

Figure 13:
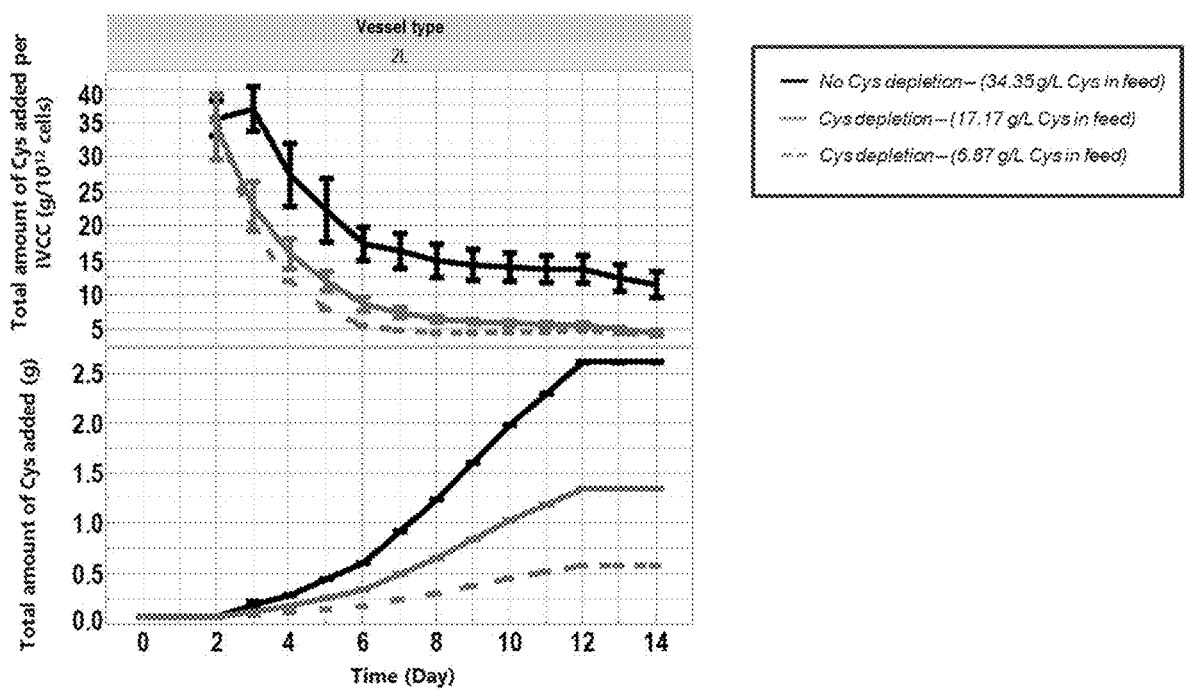
FIG. 13: Total amount of cysteine or cysteine added and Total amount of cysteine or cysteine added per IVCC for conditions described in Table 6.
Figures 14A, 14B, 14C:
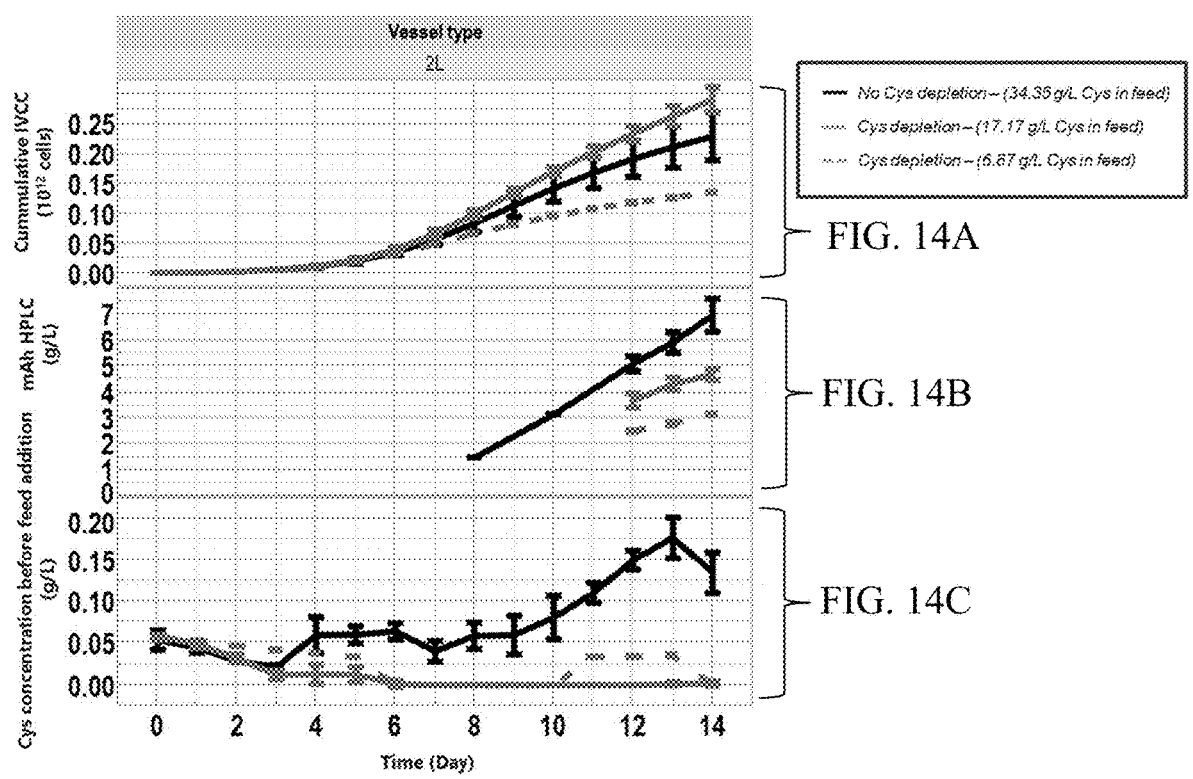
FIGS. 14A-14C: Impact of cysteine or cystine depletion on cell growth and mAb titer. The viable cell concentration (VCC) profile (FIG. 14A), the mAb titers (FIG. 14B) and the Cys concentrations before feed addition (FIG. 14C) are shown as a function of three experimental conditions: without depletion of cysteine or cystine throughout the production phase [No depletion –(34.35 g/L Cys in feed)] and two conditions with daily cysteine or cystine depletion starting on day 6 until the end of the fed-batch production and with concentration of Cys in the feed of 17.17 g/L and 6.87 g/L.

It was hypothesized that the depletion of cysteine or cystine may have an impact on the growth and productivity of a CHO cell line expressing mAb1. Nine experimental conditions in 2L bioreactors were analyzed (Table 6a): three control conditions with no depletion of cysteine or cystine throughout the production phase process, two experimental conditions with daily depletions starting on day 6 and continuing until the end of the fed-batch production process with a cysteine or cystine concentration in the feed of 6.87 g/L and four experimental conditions with depletion of cysteine or cystine on day 6 and with a cysteine or cystine concentration in the feed of 17.17 g/L. The depletions are cyclic due to the daily addition of cysteine or cystine. The feeding strategy is described in Table 6b. The total amount of cysteine or cysteine added and the total amount of cysteine or cysteine added per IVCC is depicted in FIG. 13. Cys concentrations before feed addition are shown in FIG. 14C. As shown in FIG. 14A, depletion of cysteine or cystine on day 6 does not impact cell growth if the cysteine or cystine concentration in the feed is around 17.17 g/L. Without wishing to be bound by theory, it is believed that cysteine or cystine related metabolites are accumulated and stored within the cells and are available when cysteine or cystine is depleted. However, the cell line productivity of mAb1 is impacted by the depletion of cysteine or cysteine (FIG. 14B)

TABLE 6a

| Bioreactor ID | Cys concentration in feed added (g/L) | Total amount of Cys added per IVCC on day 14 (g/$10^{12}$ cells) |
|---|---|---|
| 68 | 34.35 | 12.24 |
| 69 | 34.35 | 13.10 |
| 70 | 34.35 | 9.51 |
| 71 | 6.87 | 4.32 |
| 72 | 6.87 | 4.29 |
| 73 | 17.17 | 4.69 |
| 74 | 17.17 | 5.07 |
| 75 | 17.17 | 4.59 |
| 76 | 17.17 | 4.24 |

TABLE 6b

| Day of culture | Feed quantity added (% CSV/24 hours) |
|---|---|
| 0 | 0 |
| 1 | 0 |
| 2 | 0 |
| 3 | 0.2 |
| 4 | 0.28 |
| 5 | 0.36 |
| 6 | 0.36 |
| 7 | 0.68 |
| 8 | 0.68 |
| 9 | 0.84 |
| 10 | 0.84 |
| 11 | 0.72 |
| 12 | 0.72 |
| 13 | 0 |
| 14 | 0 |

Example 6

Figures 15A, 15B, 15C:
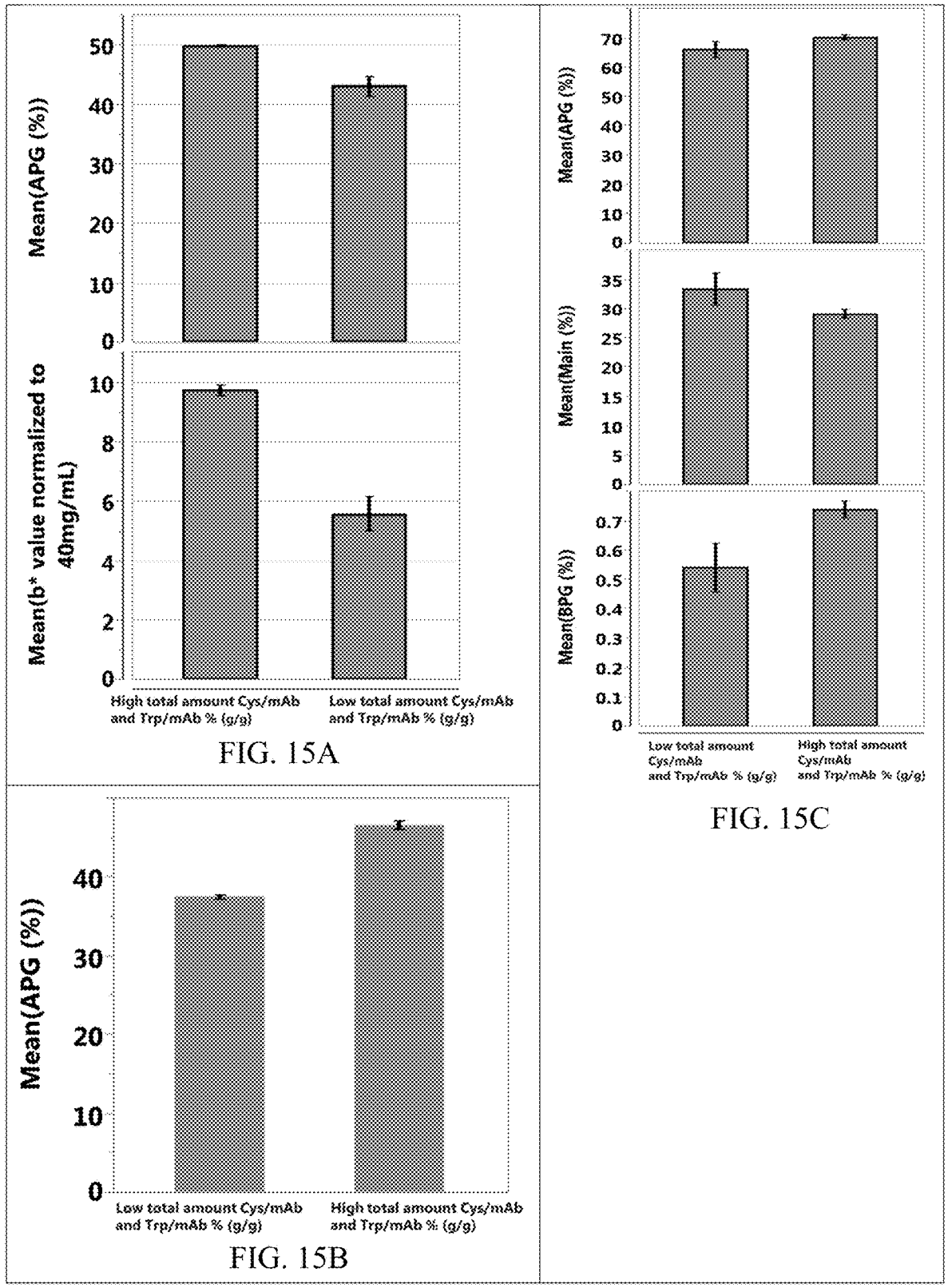
FIGS. 15A-15C: Impact of cysteine or cystine and tryptophan total quantity added wt % of total recombinant antibody produced by weight on FIG. 15A APG and b* value normalized to 40 mg/mL variant for mAb2.

The effect of the reduction of heterogeneity caused by controlling the total quantity of cysteine or cystine and tryptophan added throughout a production phase wt % of total recombinant mAb is not exclusive of mAb1, experiments on the total quantity of cysteine or cystine and tryptophan added were tested with three other CHO cell lines also producing recombinant antibodies (Table 7). As shown in FIG. 15A, an increase of APG charge variant and colour intensity are correlated to an increase of total quantity of cysteine or cystine and tryptophan added wt % of total mAb2. Similar results were obtained when analysing the APG charge variant for mAb3(FIG. 15B). Finally, an increase of APG and BPG charge variants and a decrease in main peak correlated to an increase of total quantity of cysteine or cystine and tryptophan added wt % of total mAb4(FIG. 15C). These results confirm the results obtained for mAb1.

TABLE 7

| Bioreactor ID | mAb | Total amount Cys/mAb % (g/g) | Total amount Trp/mAb % (g/g) |
|---|---|---|---|
| 77 | mAb2 | 24.02 | 14.89 |
| 78 | mAb2 | 53.01 | 29.09 |
| 79 | mAb2 | 33.35 | 21.81 |
| 80 | mAb2 | 58.67 | 32.26 |
| 81 | mAb3 | 15.97 | 17.25 |
| 82 | mAb3 | 10.92 | 16.26 |
| 83 | mAb4 | 81.15 | 57.12 |
| 84 | mAb4 | 170.18 | 62.51 |
| 85 | mAb4 | 151.22 | 55.55 |
| 86 | mAb4 | 85.45 | 60.14 |

Example 7

Figure 16A:
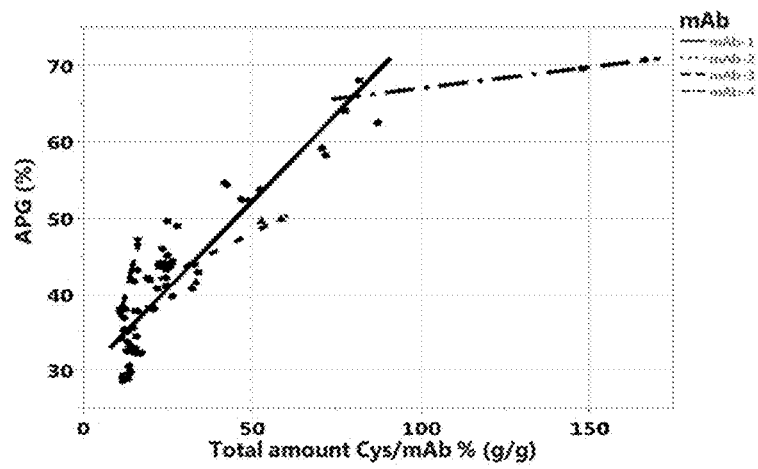
FIGS. 16A-16B: Impact of cysteine or cystine and tryptophan total quantity added wt % of total recombinant mAb1, mAb2, mAb3 and mAb4 produced weight on APG.
Figure 16B:
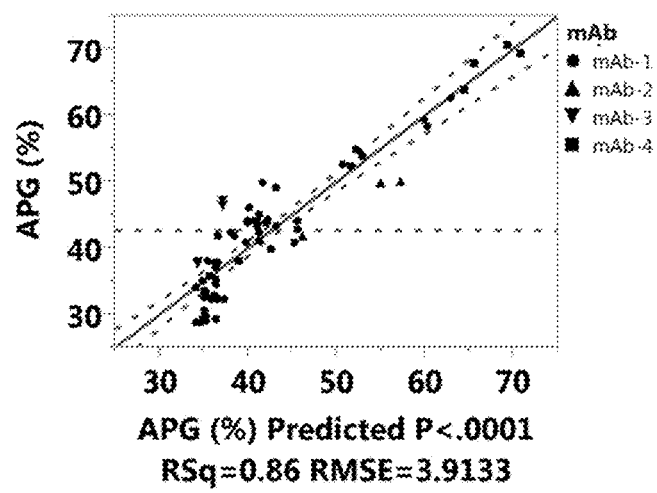

The impact of the total quantity of cysteine or cystine and tryptophan added throughout the 14 days of production wt % of total recombinant mAb weight produced was analysed based on data of the four different monoclonal antibodies tested herein (Tables 3 and 7). As shown in FIGS. 16A and 16B, the APG charge variant increase is correlated to an increase of total quantity of cysteine or cystine and tryptophan added wt % of total recombinant antibody weight produced for all four antibodies analysed. The results confirm that the relationship between the total quantity of cysteine or cystine and tryptophan added wt % of total recombinant antibody weight produced and the heterogeneity of an antibody is not confined to a specific antibody but applies to any antibody.

Example 8

Liquid Pharmaceutical Formulations

Pharmaceutical formulations of the monoclonal antibody mAb1 were manufactured in fed-batch mode at large scale, i.e. in a 2000 L stainless steel bioreactor, under standard operating conditions described in material and methods with various cysteine or cystine and tryptophan total quantity added as specified in Table 9. The buffer of the antibody sample was replaced with a diafiltration buffer (33 mM His and 250 mM Pro, pH 5.6) by at least 7 times (7 diavolumes) followed by ultrafiltration using a membrane having a Molecular Weight Cut Off (MWCO) of 30 kDa. Polysorbate 80 at the required concentration (0.03% w/v based on the final concentration) was added once the concentration of the antibody (140 mg/ml+/−14 mg/ml) was achieved. The concentration of the antibody was measured using UV A280.

Table 8 shows the appearance of charge variants of the formulated mAb1. In two productions defined as "Higher Cys addition" in Table 8 and 9 with higher cysteine or cystine total quantity added wt % of total recombinant mAb1 produced than the three other productions are defined as "Lower Cys addition" in table 8 and 9. The APG charge variant increase is correlated to an increase of total quantity of cysteine or cystine added wt % of total recombinant mAb1 produced.

TABLE 8

| | Higher Cys addition (run #1) | Higher Cys addition (run #2) | Lower Cys addition (run #1) | Lower Cys addition (run #2) | Lower Cys addition (run #3) |
|---|---|---|---|---|---|
| iCE % APG | 50.4% | 45.5% | 38.2% | 36.4% | 41.3% |
| iCE % Main Peak | 40.6% | 44.7% | 54.6% | 54.9% | 48.7% |
| iCE % BPG | 9.0% | 9.8% | 7.2% | 8.7% | 9.9% |
| Total amount Cys/mAb1 wt % (g/g) | 15.66 | 14.10 | 12.20 | 12.36 | 12.77 |
| Total amount Trp/mAb1 wt % (g/g) | 8.89 | 8.00 | 8.13 | 8.22 | 8.50 |

Example 9

Figures 17, 18:
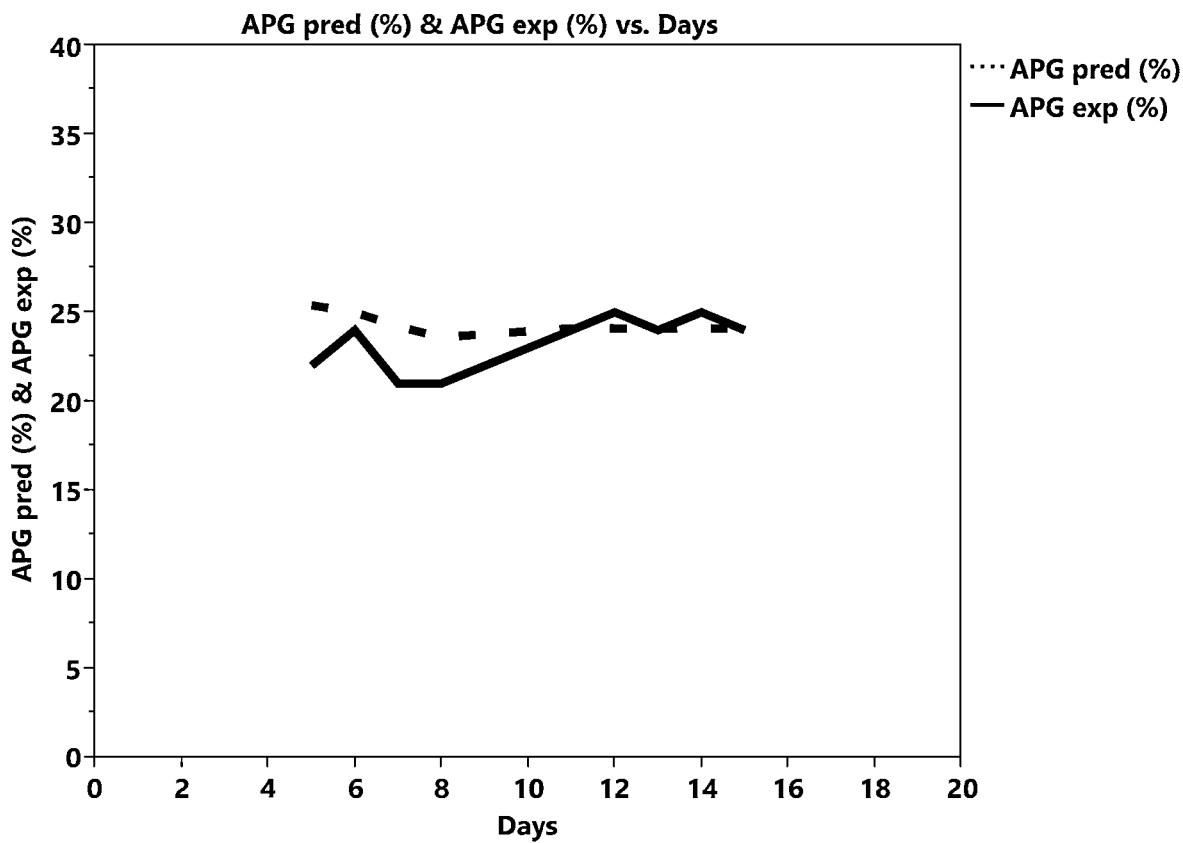
FIG. 17: Equation was developed in order to predict acidic peak group (APG) level based on data of a DG44 CHO cell line expressing mAb1 antibodies (Table 3).
FIG. 18: Comparison of experimental acidic peak group (APG) level (APG exp) with predicted APG level (APG pred) of a DG44 CHO cell line expressing mAb1 antibodies. Data were generated in perfusion production process using Alternating Tangential Flow (ATF) technology in 2L bioreactors. Prediction of APG was based on equation from FIG. 17.

A model to predict acidic peak group (APG) level was developed based on data (Tables 3) of a DG44 CHO cell line expressing mAb1 antibodies (FIG. 17). The APG is expressed as a function of the total quantity of cysteine or cystine and tryptophan added throughout the 14 days of production wt % of total recombinant mAb weight produced using Michealis Menten kinetic.

In order to apply the model to perfusion production, each perfusion production day was defined as a new production batch. Therefore, the ratios of the total amounts of cysteine or cysteine and/or tryptophan used are calculated according to the perfusion flow rate versus the rate of removal of recombinant protein produced from the production vessel. A perfusion production was performed in 2 L bioreactors using Alternating Tangential Flow (ATF) technology. As shown in FIG. 18, the APG charge variant prediction fits well with the experimental data. The results confirm that the relationship between the total quantity of cysteine or cystine and tryptophan added wt % of total recombinant antibody weight produced and the heterogeneity of an antibody can be extended to other production mode, such as perfusion, batch or chemostat mode productions.

The invention claimed is:

1. A process for producing a recombinant protein comprising:
   a) culturing host cells capable of producing a recombinant protein in a medium free of animal-derived products, wherein the host cells are CHO cells;
   b) supplementing the culture during production phase with
   cysteine or cystine in a total amount of from wt %12 wt % to 28 wt % of the expected total amount of recombinant protein produced; and
   tryptophan in a total amount of from 8 wt % to 30 wt % of the expected total amount of recombinant protein produced,
   c) and, optionally, recovering the recombinant protein from the cell culture medium wherein the recombinant protein is an antibody or an antigen-binding fragment thereof, wherein the recombinant protein is produced by the cells during said production phase, and wherein one or more initial experiments are performed to determine the expected total amount of recombinant protein produced.

2. The process according to claim 1, wherein the culture is supplemented with cysteine or cystine in a total amount of from 12 wt % to 25 wt % of the expected total amount of recombinant protein produced.

3. The process according to claim 1, wherein the culture is supplemented with tryptophan in a total amount of from 8 wt % to 25 wt % of the expected total amount of recombinant protein produced.

4. The process according to claim 1, wherein the total amount of cysteine or cystine and tryptophan in the culture is reached by adding cysteine or cystine and tryptophan to the cell culture medium:
   a) at the beginning of the production phase,
   b) once or multiple times at any time point during the production phase,
   c) through continuous addition during the production phase, or
   d) in any combination of a), b) and c).

5. The process according to claim 1, wherein the process is a batch process or a fed-batch process.

6. The process according to claim 1, wherein cysteine or cystine and tryptophan are provided through daily addition during the production phase.

7. The process according to claim 1, wherein the production phase is performed for at least 7 days.

8. The process according to claim 1, wherein the antibody or antigen-binding fragment thereof is:
   1) an antibody or antigen-binding fragment thereof which
      a) comprises CDR-H1 having the sequence as defined in SEQ ID NO: 1; CDR-H2 having the sequence as defined in SEQ ID NO: 2; CDR-H3 having the sequence as defined in SEQ ID NO: 3; CDR-L1 having the sequence as defined in SEQ ID NO: 4; CDR-L2 having the sequence as defined in SEQ ID NO: 5 and CDR-L3 having the sequence as defined in SEQ ID NO: 6; or
      b) comprises a light variable region having the sequence as defined in SEQ ID NO: 7 and a heavy variable region having the sequence as defined in SEQ ID NO: 8; or
      c) comprises a light variable region having at least 80% identity or similarity to the sequence as defined in SEQ ID NO: 7 and a heavy variable region having at least 80% identity or similarity to the sequence as defined in SEQ ID NO: 8; or
      d) comprises a light variable region having the sequence as defined in SEQ ID NO: 7 and a heavy chain having the sequence as defined in SEQ ID NO: 11; or
      e) comprises a light variable region having at least 80% identity or similarity to the sequence as defined in SEQ ID NO: 7 and a heavy chain having at least 80% identity or similarity to the sequence as defined in SEQ ID NO: 11; or
   2) an antibody which comprises a light chain having the sequence as defined in SEQ ID NO: 9 and a heavy chain having the sequence as defined in SEQ ID NO: 10; or
   3) an antibody which comprises a light chain having at least 80% identity or similarity to the sequence as defined in SEQ ID NO: 9 and a heavy chain having at least 80% identity or similarity to the sequence as defined in SEQ ID NO: 10.

9. The process according to claim 1, wherein the production phase is carried out in a bioreactor with a volume of equal or more than 50 L.

10. The process according to claim 1, wherein the process comprises the step of recovering the recombinant protein from the cell culture medium and a further step of purifying the recombinant protein.

11. The process according to claim 10, wherein the purification comprises Protein A chromatography.

12. The process according to claim 10, further comprising the step of formulating the purified recombinant protein.

13. The process according to claim 10, wherein the recombinant protein is formulated in a liquid formulation comprising one or more amino acids and a surfactant.

14. The process according to claim 13, wherein the formulation comprises histidine and/or proline.

15. The process according to claim 14, wherein the formulation is at a pH of between 5 and 7.4 and comprises histidine in a concentration of 5 mM to 100 mM, and/or proline in a concentration of 100 mM to 500 mM.

16. The process according to claim 15, wherein the formulation comprises histidine in a concentration of 30 mM and proline in a concentration of 250 mM and is at a pH between 5.2 and 6.0.

17. The process according to claim 13, wherein the surfactant is polysorbate 80 in a concentration of 0.001% to 0.1% (w/v).

18. The process according to claim 13, wherein the recombinant protein is an antibody and the antibody is formulated at a concentration of 10 mg/ml to 250 mg/ml.

19. The process according to claim 1, wherein the process reduces the heterogeneity of the recombinant proteins produced, wherein said reduction of heterogeneity comprises reducing:
   a) charge heterogeneity; and/or
   b) amino acid oxidation, isomerization, fragmentation, other covalent adducts, glycation, deamidation, cysteinylation; and/or
   c) colour or intensity of colour between different batches of the recombinant protein;
   and/or d) high molecular weight species (HMWS); and/or
   e) recombinant protein instability.

20. The method according to claim 1, said one or more initial experiments comprising culturing the host cells of step a) under conditions allowing for the production of recombinant protein and determining the expected total amount of recombinant protein produced by the cultured cells.

* * * * *